(12) United States Patent
Liu et al.

(10) Patent No.: US 12,347,581 B2
(45) Date of Patent: Jul. 1, 2025

(54) COLLIMATOR ASSEMBLY AND OPERATING METHOD THEREOF

(71) Applicant: SHANGHAI UNITED IMAGING HEALTHCARE CO., LTD., Shanghai (CN)

(72) Inventors: Yanfang Liu, Shanghai (CN); Yifeng Wang, Shanghai (CN); Cheng Ni, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 444 days.

(21) Appl. No.: 17/649,057

(22) Filed: Jan. 26, 2022

(65) Prior Publication Data

US 2022/0148754 A1 May 12, 2022

Related U.S. Application Data

(63) Continuation of application No. PCT/CN2020/097346, filed on Jun. 22, 2020.

(30) Foreign Application Priority Data

Jul. 26, 2019 (WO) ................. PCT/CN2019/097998

(51) Int. Cl.
*G21K 1/02* (2006.01)
*A61N 5/10* (2006.01)
(52) U.S. Cl.
CPC ............. *G21K 1/02* (2013.01); *A61N 5/1045* (2013.01)

(58) Field of Classification Search
CPC ......... G21K 1/02; G21K 1/046; A61N 5/1045
USPC ........................................ 250/505.1; 378/150
See application file for complete search history.

(56) References Cited

U.S. PATENT DOCUMENTS

| 5,144,647 | A | 9/1992 | Kikuchi |
| 5,591,983 | A | 1/1997 | Yao |
| 6,266,393 | B1 | 7/2001 | Ein-Gal |

(Continued)

FOREIGN PATENT DOCUMENTS

| AU | 2017208382 A1 | 8/2017 |
| CN | 109224318 A | 1/2019 |
| EP | 2687259 A1 | 1/2014 |

OTHER PUBLICATIONS

International Search Report in PCT/CN2019/097998 mailed on Apr. 26, 2020, 5 pages.

(Continued)

*Primary Examiner* — Michael Maskell
(74) *Attorney, Agent, or Firm* — METIS IP LLC

(57) ABSTRACT

The present disclosure may provide a collimator assembly. The collimator assembly may include a multi-leaf collimator (MLC) situated in a first plane and at least one block situated in a second plane different from the first plane. The MLC may include at least one first group of leaves and at least one second group of leaves opposing each other and being moveable along a first direction. One of the at least one block may be located at a position corresponding to an end of the at least one first group of leaves. Projection of one of the at least one block along a second direction may partially overlap projection of the at least one first group of leaves along the second direction.

18 Claims, 15 Drawing Sheets

(56) References Cited

U.S. PATENT DOCUMENTS

| | | | |
|---|---|---|---|
| 6,459,769 B1 * | 10/2002 | Cosman | G21K 1/04 378/65 |
| 6,600,810 B1 | 7/2003 | Hughes | |
| 8,067,751 B2 * | 11/2011 | Mohr | G21K 1/04 378/65 |
| 9,443,633 B2 * | 9/2016 | Orton | A61N 5/1045 |
| 10,518,110 B1 | 12/2019 | Jimenez-Carvajal et al. | |
| 2001/0043669 A1 * | 11/2001 | Ein-Gal | G21K 1/046 378/150 |
| 2008/0073591 A1 | 3/2008 | Mohr | |
| 2008/0165930 A1 | 7/2008 | Perkins | |
| 2012/0012763 A1 * | 1/2012 | Kuusela | G21K 1/046 378/150 |
| 2012/0043482 A1 * | 2/2012 | Prince | G21K 1/046 250/505.1 |
| 2012/0105969 A1 * | 5/2012 | Ehringfeld | A61N 5/1048 359/641 |
| 2012/0256103 A1 | 10/2012 | Luzzara | |
| 2014/0112453 A1 | 4/2014 | Prince et al. | |
| 2015/0273239 A1 | 10/2015 | Hsu et al. | |
| 2017/0084359 A1 * | 3/2017 | Constantin | A61N 5/1045 |
| 2017/0087386 A1 | 3/2017 | Mellenberg et al. | |
| 2017/0143995 A1 | 5/2017 | Bergfjord | |
| 2017/0148536 A1 | 5/2017 | Kawrykow et al. | |
| 2018/0078784 A1 * | 3/2018 | Schnarr | A61N 5/1031 |
| 2018/0161602 A1 | 6/2018 | Kawrykow et al. | |
| 2018/0261351 A1 | 9/2018 | Kawrykow et al. | |
| 2019/0001153 A1 | 1/2019 | Jones et al. | |
| 2019/0046815 A1 * | 2/2019 | Ollila | A61N 5/1031 |
| 2019/0175944 A1 | 6/2019 | Towe et al. | |
| 2019/0209864 A1 | 7/2019 | Stahl et al. | |
| 2019/0240209 A1 * | 8/2019 | Kwon | A61K 9/2846 |
| 2019/0240509 A1 | 8/2019 | Kuusela et al. | |
| 2020/0185119 A1 | 6/2020 | Stahl et al. | |

OTHER PUBLICATIONS

Written Opinion in PCT/CN2019/097998 mailed on Apr. 26, 2020, 4 pages.
International Search Report in PCT/CN2020/097346 mailed on Sep. 25, 2020, 5 pages.
Written Opinion in PCT/CN2020/097346 mailed on Sep. 25, 2020, 5 pages.

* cited by examiner

COLLIMATOR ASSEMBLY AND OPERATING METHOD THEREOF

CROSS-REFERENCE TO THE RELATED APPLICATIONS

This application is a continuation of International Patent Application No. PCT/CN2020/097346, filed on Jun. 22, 2020, which claims priority of International Application No. PCT/CN2019/097998 filed on Jul. 26, 2019, the contents of each of which are hereby incorporated by reference.

TECHNICAL FIELD

The present disclosure generally relates to radiotherapy, and more specifically relates to a collimator assembly and a method for operating the collimator assembly.

BACKGROUND

Radiotherapy is generally part of cancer treatment to control or kill, e.g., a tumor of an object, using ionizing radiation. A multi-leaf collimator (MLC) may be used to shape radiation to fit the shape of the tumor so that the tumor receives sufficient radiation. For instance, by moving at least one leaf of the MLC to at least one desired position, a treatment region conforming to the shape of the tumor may be formed. In some cases, the MLC is likely to fail to block pathways of leaking radiation within a region other than the region of the tumor while moving the at least one leaf, which may cause damage to the normal tissues of the object. Besides, a resolution of the treatment region may be limited by the sizes of the leaves of the MLC, e.g., the widths of the leaves. Thus, it is desirable to provide a collimator assembly and/or a method for operating the collimator assembly to more effectively block pathways of leaking radiation other than in a treatment region and/or improving a resolution of the treatment region.

SUMMARY

According to one aspect of the present disclosure, a collimator assembly may be provided. The collimator assembly may include a multi-leaf collimator (MLC) situated in a first plane and at least one block situated in a second plane different from the first plane. The MLC may include at least one first group of leaves and at least one second group of leaves opposing each other and being moveable along a first direction. One of the at least one block may be located at a position corresponding to an end of the at least one first group of leaves. Projection of one of the at least one block along a second direction may partially overlap projection of the at least one first group of leaves along the second direction.

In some embodiments, the projection of the one of the at least one block along the second direction may at least cover projection of rear ends of the at least one first group of leaves along the second direction.

In some embodiments, the collimator assembly may further include at least one jaw situated in the second plane. The at least one jaw may span at least a part of the at least one first group of leaves and the at least one second group of leaves.

In some embodiments, the at least one block may be fixed at the position.

In some embodiments, the at least one block may be moveable with respect to the position.

In some embodiments, the at least one block may further include a second block situated in the second plane. The second block may be located at a position corresponding to an end of the at least one second group of leaves. Projection of the second block may partially overlap projection of the at least one second group of leaves along the second direction.

In some embodiments, projection of the second block along the second direction may at least cover projection of rear ends of the at least one second group of leaves along the second direction.

In some embodiments, a length of each leaf of the MLC may be smaller than or equal to a half of a length of a radiation area associated with the collimator assembly.

In some embodiments, one or more leaves of the MLC may be configured to move to a centerline of the radiation area.

In some embodiments, a size of each of the at least one block may relate to at least one of: a first reference distance that at least one leaf of the at least one first group of leaves is allowed to move, a second reference distance that at least one leaf of the at least one second group of leaves is allowed to move, a width of at least one leaf of the at least one first group of leaves, a width of at least one leaf of the at least one second group of leaves, a length of at least one leaf of the at least one first group of leaves, or a length of at least one leaf of the at least one second group of leaves.

In some embodiments, at least one of leaves of the MLC may be movable to form a treatment region associated with the collimator assembly.

In some embodiments, the at least one jaw may be movable along a third direction. The third direction may be orthogonal to the first direction and the second direction.

In some embodiments, a gap may exist between projection of the at least one jaw along the second direction and the treatment region.

In some embodiments, projection of the at least one jaw along the second direction may partially overlap the treatment region.

In some embodiments, a resolution of the treatment region may be adjustable by moving the at least one jaw.

In some embodiments, the at least one jaw may include a first jaw and a second jaw that are situated in the second plane.

In some embodiments, the second plane may be below the first plane along the second direction.

In some embodiments, the second plane may be above the first plane along the second direction.

In some embodiments, at least one radiation non-resistant component of the collimator assembly may be situated between the MLC and at least one of the at least one block or the at least one jaw.

In some embodiments, the collimator assembly may further include at least one second jaw being moveable along the first direction.

According to another aspect of the present disclosure, a radiation treatment system may be provided. The radiation treatment system may include a radiation source, a multi-leaf collimator (MLC) situated in a first plane, and at least one block situated in a second plane different from the first plane. The radiation source may be configured to emit radiation beams. The MLC may include at least one first group of leaves and at least one second group of leaves opposing each other and being moveable along a first direction. One of the at least one block may be located at a position corresponding to an end of the at least one first group of leaves. Projection of one of the at least one block along a second direction may partially overlap projection of the at least one first group of leaves along the second direction. The MLC and the at least one block may shield a portion of the radiation beams.

According to another aspect of the present disclosure, a collimator assembly may be provided. The collimator assembly may include a multi-leaf collimator (MLC) situated in a first plane and at least one jaw situated in a second plane different from the first plane. The MLC may include at least one first group of leaves and at least one second group of leaves opposing each other and being moveable along a first direction to form a treatment region. Projection of the at least one jaw along a second direction may partially overlap the treatment region.

In some embodiments, a resolution of the treatment region may be adjustable by moving the at least one jaw.

According to another aspect of the present disclosure, a radiation treatment system may be provided. The radiation treatment system may include a radiation source, a multi-leaf collimator (MLC) situated in a first plane, and at least one jaw situated in a second plane different from the first plane. The radiation source may be configured to emit radiation beams within a radiation area. The MLC may include at least one first group of leaves and at least one second group of leaves opposing each other and being moveable along a first direction to form a treatment region. Projection of the at least one jaw along a second direction may partially overlap the treatment region. The MLC and the at least one jaw may shield a portion of the radiation beams.

According to another aspect of the present disclosure, a method for operating a multi-leaf collimator (MLC) may be provided. The method may be implemented on a computing device having at least one processor and at least one computer-readable storage device. The MLC may include at least a first layer of leaves and a second layer of leaves. Each of the first layer of leaves and the second layer of leaves may include a first group of leaves and a second group of leaves. At least a portion of the leaves may be movable to form a treatment region by blocking pathways of a first portion of radiation beams within a radiation area associated with the MLC. A second portion of the radiation beams may impinge on the treatment region. The method may include: determining whether a first region exists, wherein the first region forms when one or more leaves of the first group of the first layer of leaves pass across a first line such that the first region is exposed to allow at least a portion of the first portion of the radiation beams to leak through; and causing, based on a determination result, the second layer of leaves of the MLC to operate.

In some embodiments, the first line may be a centerline of the radiation area. A length of at least one of the first group of leaves may be equal to a half of a length of the radiation area.

In some embodiments, the determination result may include that the first region exists, and the causing the second layer of leaves of the MLC to operate may include: causing one or more leaves of the second layer of leaves to move to shield at least a portion of radiation beams leaked through the first region.

In some embodiments, the determination result may include that the first region does not exist, and the causing the second layer of leaves of the MLC to operate may include: causing one or more leaves of the second layer of leaves to move to block a part of the second portion of the radiation beams.

According to another aspect of the present disclosure, a method for operating a collimator assembly may be provided. The method may be implemented on a computing device having at least one processor and at least one computer-readable storage device. The collimator assembly may include a multi-leaf collimator (MLC) and at least one block, the MLC includes at least a first layer of leaves and a second layer of leaves. Each of the first layer of leaves and the second layer of leaves may include a first group of leaves and a second group of leaves. At least a portion of the leaves may be movable to form a treatment region by blocking pathways of a first portion of radiation beams within a radiation area associated with the collimator assembly. A second portion of the radiation beams may impinge on the treatment region. The method may include: determining whether a first region exists, wherein the first region forms when one or more leaves of the first group of the first layer of leaves pass across a first line such that the first region is exposed to allow at least a portion of the first portion of the radiation beams to leak through; and causing, based on a determination result, at least one of the at least one block or the second layer of leaves of the MLC to operate.

In some embodiments, the at least one block may be fixed in a second plane, and projection of the at least one of the at least one block may at least partially overlaps the MLC.

In some embodiments, the determination result may include that the first region exists, and the causing at least one of the at least one block or the second layer of leaves of the MLC to operate may include: causing one or more leaves of the second layer of leaves to move to block a part of the second portion of the radiation beams.

In some embodiments, the at least one block may be moveable, the determination result may include that the first region exists, and the causing at least one of the at least one block or the second layer of leaves of the MLC to operate may include: determining whether the at least one block is able to move; and causing, based on a second determination result, the second layer of leaves to operate.

In some embodiments, the causing, based on a second determination result, the second layer of leaves to operate may include: in response to the second determination that the at least one block is able to move, causing the at least one block to shield at least a portion of the radiation beams that leak through the first region, and causing one or more leaves of the second layer of leaves to move to block a part of the second portion of the radiation beams.

In some embodiments, the causing, based on a second determination result, the second layer of leaves to operate may include: in response to the second determination that the at least one block is unable to move, causing one or more leaves of the second layer of leaves to shield at least a portion of the radiation beams that leak through the first region.

In some embodiments, the determination result may include that the first region does not exist, and the causing at least one of the at least one block or the second layer of leaves of the MLC to operate may include: causing one or more leaves of the second layer of leaves to move to block a part of the second portion of the radiation beams.

According to another aspect of the present disclosure, a non-transitory computer readable medium may be provided. The non-transitory computer readable medium may include instructions being executed by at least one processor, causing the at least one processor to implement a method for operating a multi-leaf collimator (MLC). The MLC may include at least a first layer of leaves and a second layer of leaves. Each of the first layer of leaves and the second layer of leaves may include a first group of leaves and a second group of leaves. At least a portion of the leaves may be movable to form a treatment region by blocking pathways of a first portion of radiation beams associated with the MLC. A second portion of the radiation beams may impinge on the treatment region. The method may include: determining whether a first region exists, wherein the first region forms when one or more leaves of the first group of the first layer of leaves pass across a first line such that the first region is exposed to allow at least a portion of the first portion of the radiation beams to leak through; and causing, based on a determination result, the second layer of leaves of the MLC to operate.

According to another aspect of the present disclosure, a non-transitory computer readable medium may be provided. The non-transitory computer readable medium may include instructions being executed by at least one processor, causing the at least one processor to implement a method for operating a collimator assembly. The collimator assembly may include a multi-leaf collimator (MLC) and at least one block. The MLC may include at least a first layer of leaves and a second layer of leaves. Each of the first layer of leaves and the second layer of leaves may include a first group of leaves and a second group of leaves. At least a portion of the leaves may be movable to form a treatment region by blocking pathways of a first portion of radiation beams associated with the collimator assembly. A second portion of the radiation beams may impinge on the treatment region. The method may include: determining whether a first region exists, wherein the first region forms when one or more leaves of the first group of the first layer of leaves pass across a first line such that the first region is exposed to allow at least a portion of the first portion of the radiation beams to leak through; and causing, based on a determination result, at least one of the at least one block or the second layer of leaves of the MLC to operate.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
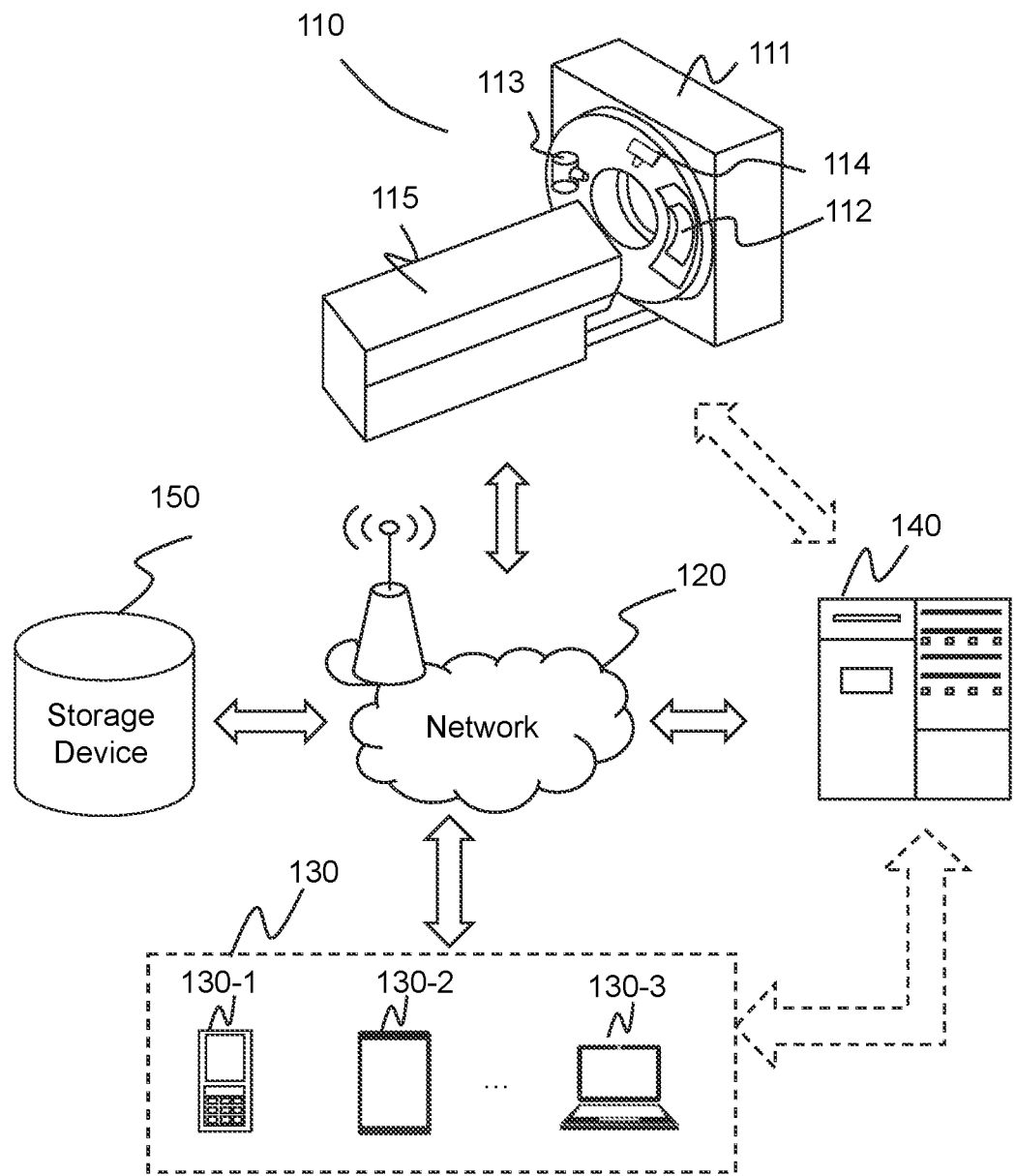
FIG. 1 is a schematic diagram illustrating an exemplary radiation treatment system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. The term "direction" may include the opposite direction of the direction and a plurality of directions that are parallel to the direction. The term "plane" may include both planar and curved or cylindrical planes. The direction may include both linear and arc trajectories. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, unless otherwise defined, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Figure 6A:
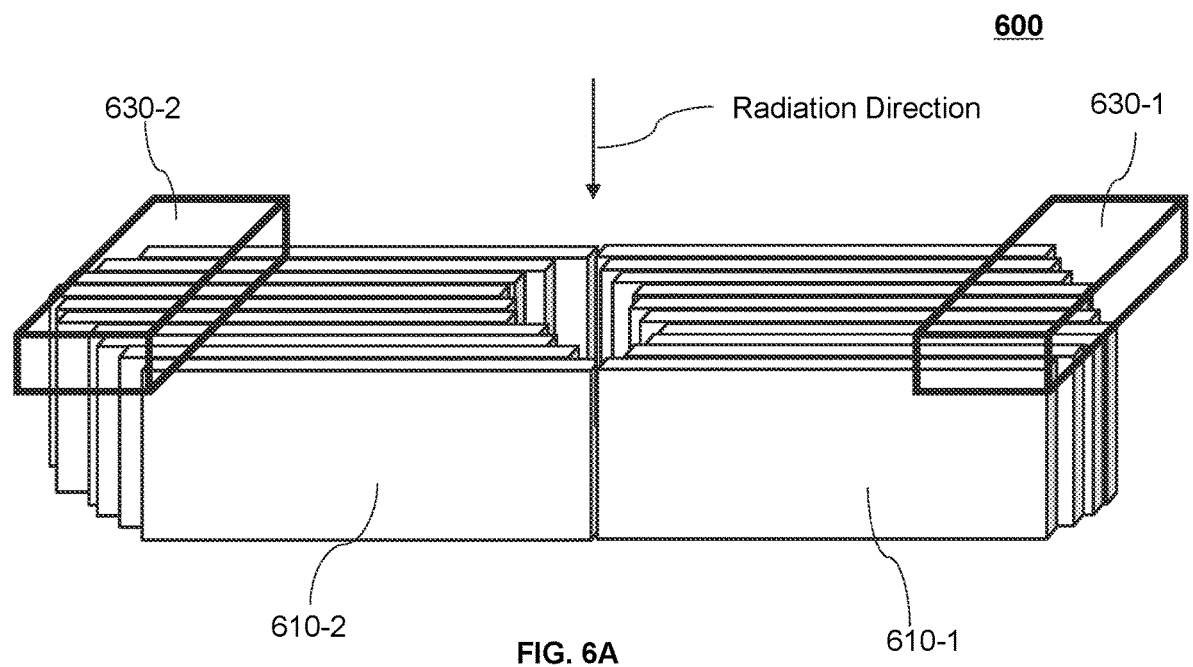
FIG. 6A is a schematic diagram illustrating an exemplary collimator assembly according to some embodiments of the present disclosure
Figure 6B:
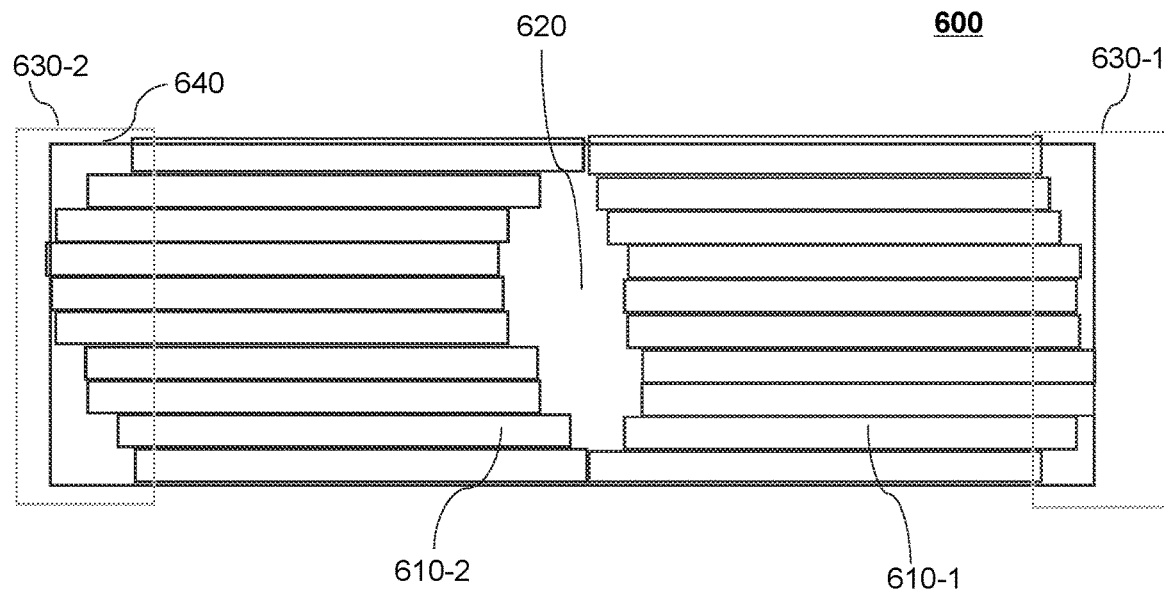
FIG. 6B is a section view illustrating an exemplary collimator assembly according to some embodiments of the present disclosure.

A first aspect of the present disclosure relates to a collimator assembly. The collimator assembly may include a multi-leaf collimator (MLC) situated in a first plane and at least one block situated in a second plane other than the first plane. The MLC may include at least one first group of leaves and at least one second group of leaves opposing each other and being moveable along a first direction (e.g., the x-direction illustrated in FIG. 4A). The at least one block may include a block located at a position corresponding to a rear end (e.g., the rear end 414 illustrated in FIG. 4A) of the at least one first group of leaves so that the projection of the block along a second direction (e.g., a radiation direction 405 illustrated in FIG. 4A) partially overlaps the projection of the at least one first group of leaves along the second direction. As used herein, a front end of a leaf of a collimator assembly refers to the end of the leaf that participates in forming an aperture of the collimator assembly corresponding to a treatment region formed by radiation traversing the collimator assembly. As used herein, a rear end of a leaf of a collimator assembly refers to the end of the leaf that is opposite to the front end along the longitudinal direction (also referred to as "first direction") (e.g., the x-direction illustrated in FIG. 4A) of the leaf. A front end of a leaf may be located closer to the centerline of a radiation ray and/or the centerline of the radiation area/treatment region formed by a radiation ray traversing the collimator than the rear end of the leaf. In some embodiments, the at least one block may also include a second block located at a position corresponding to a rear end of the at least one second group of leaves so that the projection of the block along the second direction partially overlaps the projection of the at least one second group of leaves along the second direction. In some embodiments, there may be no gap between the projection of the block along the second direction and the projection of the at least one first group of leaves along the second direction and no gap between the projection of the second block along the second direction and the projection of the at least one second group of leaves along the second direction. That is, the projection of the block may at least cover the projection of rear ends of the at least one first group of leaves as illustrated in FIG. 6A; the projection of the second block may at least cover the projection of rear ends of the at least one second group of leaves as illustrated in FIG. 6B. For example, if the MLC fails to block pathways of leaking radiation beams within an end area in a radiation area associated with the collimator assembly while moving at least one leaf of the MLC to form a treatment region, the at least one block may be located at position(s) so that the projection of the at least one block covers the end area, thereby shielding at least a portion of the leaking radiation beams within the end area from passing through the collimator assembly.

By arranging the block(s), radiation beams delivered to a normal portion (e.g., surrounding normal tissues) of the object may be reduced, thereby reducing the relative toxicity of radiation to the surrounding normal tissues. The size of the block(s) may be relatively small, and thus occupy a little space of the collimator assembly. Besides, the weight of the block(s) may be relatively light, and thus cause a little load on the collimator assembly. In some cases, by adjusting the size of the block(s), one or more leaves of the MLC may be designed with a relatively small length and thus the one or more leaves may move more quickly, thereby shortening the time for radiation therapy.

In some embodiments, the collimator assembly described above may also include at least one jaw spanning at least a part of the at least one first group of leaves and the at least one second group of leaves. The block(s) and the jaw(s) may be situated in a same plane (i.e., the second plane), which may reduce the space occupied by the collimator assembly, and/or increase the space available for situating a patient. In some embodiments, the projection of the at least one jaw along a second direction (substantially along which a treatment beam travels from a treatment radiation source (e.g., the first radiation source 114) to the treatment region) may partially overlap the treatment region, i.e., form the treatment region together with the MLC, thereby improving the resolution of the treatment region and its adjustability. The resolution of the treatment region along the second direction may be adjustable by moving the at least one jaw.

In some embodiments, at least one radiation non-resistant component (e.g., a circuit board) of the collimator assembly may be shielded from radiation by being situated downstream (along the direction in which a radiation beam travels from the treatment radiation source (e.g., the first radiation source 114) to the treatment region) to the MLC, the at least one jaw, and/or the at least one block.

In some embodiments, a movement speed of the at least one jaw may be faster than a movement speed of the leaves of the MLC. Thus, the speed at which the at least one jaw responds for blocking a portion of the radiation beams may be faster than that of the leaves of the MLC, thereby shortening the time for radiation therapy, and/or reducing the amount of undesired radiation that leaks through the collimator assembly and/or impinges on a patient receiving the treatment.

A second aspect of the present disclosure relates to a collimator assembly. The collimator assembly may include a multi-leaf collimator (MLC) situated in a first plane and at least one jaw situated in a second plane other than the first plane. The MLC may include at least one first group of leaves and at least one second group of leaves opposing each other and being moveable along a first direction (e.g., the x-direction illustrated in FIG. 4A) to form a treatment region. The projection of the at least one jaw along a second direction (e.g., the radiation direction 405 illustrated in FIG. 4A) may partially overlap the treatment region, i.e., forming the treatment region together with the MLC, thereby improving the resolution of the treatment region and its adjustability. In some embodiments, the resolution of the treatment region along the second direction may be adjustable by moving the at least one jaw.

A third aspect of the present disclosure relates to a method for operating an MLC. The MLC may at least have a first layer of leaves and a second layer of leaves being moveable to form a treatment region by blocking pathways of a first portion of radiation beams within a radiation area associated with the MLC. A second portion of the radiation beams may impinge on the treatment region. If the first layer of leaves of the MLC fails to block pathways of leaking radiation beams within a first region other than the treatment region, one or more layers of leaves other than the first layer of leaves and the second layer of leaves of the MLC may be operated to move to form the treatment region with the first layer of leaves. At least a portion of the second layer of leaves may be operated to blocking pathways of at least a portion of the leaking radiation beams within the first region. If the first layer of leaves blocks pathways of leaking radiation beams within the first region, the one or more layers of leaves and the second layer of leaves may be operated to move to form the treatment region with the first layer of leaves.

By providing the method described above, the MLC may simultaneously form the treatment region and block pathways of at least a portion of the leaking radiation beams delivered to the normal portion of the object other than the lesion. In some cases, a boundary of the treatment region may be formed based on a plurality of steps, and at least one width of the plurality of steps may be smaller than the width of each leaf. Thus the resolution (or the fine degree) of the treatment region may be improved compared to that of a treatment region formed by the first layer of leaves.

A fourth aspect of the present disclosure relates to a method for operating a collimator assembly. The collimator assembly may include an MLC having at least two layers of leaves and at least one block. If a first layer of leaves of the MLC fails to block pathways of leaking radiation beams within a first region other than the treatment region and the at least one block is able to block at least a portion of the leaking radiation beams within the first region, one or more layers of leaves other than the first layer of leaves may be operated to move to form the treatment region with the first layer of leaves. If the first layer of leaves of the MLC fails to block the pathways of leaking radiation beams within the first region and the at least one block is unable to block the pathway of the leaking radiation beams within the first region, at least a portion of the second layer of leaves of the MLC may be operated to move to block pathways of the at least a portion of the radiation beams within the first region. If the first layer of leaves blocks pathways of leaking radiation beams within the first region, the one or more layers of leaves other than the first layer of leaves may be operated to move to form the treatment region with the first layer of leaves.

By providing the method described above, when the at least one block fails to block the at least a portion of the leaking radiation beams, at least a portion of leaves of the MLC may be operated to block the at least a portion of the leaking radiation beams, thereby ensuring the at least a portion of the leaking radiation beams not to be delivered to the normal portion of the object other than the lesion.

Some embodiments of the present disclosure may also provide a radiation treatment system. The radiation treatment system may include a radiation source configured to emit radiation beams within the radiation area and the collimator assembly described above.

FIG. 1 is a schematic diagram illustrating an exemplary radiation treatment system 100 according to some embodiments of the present disclosure. The radiation treatment system 100 may include a radiation delivery device 110, a network 120, one or more terminals 130, a processing device 140, and a storage device 150. The components of the radiation treatment system 100 may be connected in various ways. Mere by way of example, the radiation delivery device 110 may be connected to the processing device 140 through the network 120. As another example, the radiation delivery device 110 may be connected to the processing device 140 directly as indicated by the bi-directional arrow in dotted lines linking the radiation delivery device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

In some embodiments, the radiation delivery device 110 may simultaneously perform imaging and treatment on an object. Mere by way of example, the radiation delivery device 110 may include an imaging assembly, a treatment radiation source (e.g., the first radiation source 114), a gantry 111, and a table 115. The imaging assembly may include a conventional CT, a cone beam CT (CBCT), a helical CT, a multi-slice CT, a PET-CT, or the like, or any combination thereof. The imaging assembly may be configured to generate one or more images before, during or after radiotherapy. As shown in FIG. 1, the imaging assembly may include an imaging radiation source (e.g., the second radiation source 113) and a radiation detector 112 opposite to the second radiation source 113. The gantry 111 may include a rotary ring (not shown in FIG. 1). The rotary ring may be configured to accommodate the second radiation source 113, the radiation detector 112, and the first radiation source 114. In some embodiments, the first radiation source 114 may emit a first beam toward a region (e.g., a tumor) of an object that is placed on the table 115. The second radiation source 113 may emit a second beam toward a second region (e.g., an imaging region) of the object. In some embodiments, the intensity of the first beam may be different from the intensity of the second beam. For example, the energy of the first beam may be several megavolts (MV), this energy being greater than that of the second beam, which may be several kilovolts (kV). The object may be a biological object (e.g., a patient, an animal) or a non-biological object. In the present disclosure, "object" and "subject" are used interchangeably. The radiation detector 112 may be configured to detect radiation emitted from the second radiation source 113. It should be noted that the above descriptions of the radiation delivery device 110 are merely provided for the purposes of illustration, and not intended to limit the scope of the present disclosure. In some embodiments, the imaging assembly in the radiation delivery device 110 may be omitted, and the radiation delivery device 110 may include only one radiation source (e.g., the first radiation source 114) for delivering radiotherapy.

In some embodiments, the radiation delivery device 110 may include a collimator assembly (not shown in FIG. 1). The collimator assembly may be configured to collimate radiation beams within a radiation area of the first radiation source 114. In some embodiments, the radiation area may be represented by a rectangle (e.g., a rectangle 440 illustrated in FIG. 4B). The length of the radiation area may refer to a dimension of the radiation area that is parallel to a leaf moving direction (e.g., a longitudinal direction, the x-direction illustrated in FIG. 4A). The width of the radiation area may refer to a dimension of the radiation area (e.g., the y-direction illustrated in FIG. 4A) orthogonal to the direction along which a leaf moves, or referred to as a leaf moving direction (e.g., a longitudinal direction), and a radiation direction (e.g., the z-direction illustrated in FIG. 4A).

In some embodiments, the collimator assembly may form an aperture through which a portion of the radiation beams is delivered to a treatment region. The treatment region may conform to the shape of a lesion. The lesion (e.g., the tumor) of the object may be located in the treatment region for radiotherapy. In some embodiments, a center of the treatment region may be an isocenter of the radiation delivery device 110. As used herein, the isocenter of the radiation delivery device 110 may refer to a point through which central rays of the first radiation source 114 passes during radiotherapy. Thus, the lesion may receive sufficient radiation, and the damage to a normal portion (normal tissues surrounding the lesion) of the object may be reduced during the radiotherapy.

A resolution of the treatment region may be used to represent a fine degree of a boundary of a treatment region. The higher the resolution is, the finer the boundary of the treatment region may be. Generally, the shape of the lesion may be irregular, and the boundary of the treatment region (or the aperture) may be irregular. In order to better conform to the shape of the lesion, the boundary of the treatment region should have a relatively high resolution.

In some current application scenarios, the collimator assembly may include a multi-leaf collimator (MLC) having a single layer of leaves. The projection of the MLC (or the single layer of leaves) may sometimes fail to cover an end area in the radiation area, that is, the MLC (or the single layer of leaves) fails to block pathways of leaking radiation beams within the end area. As used herein, the end area may form when one or more ends corresponding to one or more leaves of a plurality of leaves included in the MLC within a boundary of the radiation area. Each of the one or more ends may refer to an end of a leaf that is relatively near to the boundary of the radiation area along a longitudinal direction.

The resolution of the treatment region (e.g., the resolution along the z-direction illustrated in FIG. 1) may relate to a width of each leaf that forms the boundary of the treatment region. The higher the width of the leave is, the smaller the resolution may be. In some cases, the resolution of the treatment region may increase by decreasing the width of each leaf, resulting in increasing the count of the leaves. By doing this, the difficulty for manufacturing the leaves of the MLC may increase and the cost for the manufacture may increase accordingly. Besides, a probability that a leaf deforms and/or a leaf or MLC breaks down may increase. More detailed descriptions of the leaking radiation beams in the end area and/or the resolution of the treatment region with respect to the MLC having the single layer of leaves can be found elsewhere in the present disclosure. See, e.g., FIGS. 4A-4B and the descriptions thereof.

In some current application scenarios, the collimator assembly may include an MLC having at least two layers of leaves. The at least two layers of leaves may move along with each another. Accordingly, if a first layer of leaves of the MLC fail to block pathways of leaking radiation beams within a first region other than the treatment region, the MLC (i.e., the at least two layers of leaves) may fail to block pathways of the leaking beams within an end area of the radiation area. As used herein, the first region may form when one or more leaves of the first (or second) group of the first layer of leaves pass across a first (or second) line such that the first region is exposed to allow at least a part of the first portion of the radiation beams to leak through. Since one or more layers of leaves other than the first layer of leaves may block pathways of at least a portion of leaking radiation beams within the first region, the end area may include at least a portion of the first region. More detailed descriptions of the leaking radiation beams in the first region or the end area with respect to the MLC having the at least two layers of leaves can be found elsewhere in the present disclosure. See, e.g., FIGS. 5A-5B and the descriptions thereof.

As described above, the treatment region may conform to the shape of the lesion. The leaking radiation beams within the end area (or the first region) may be delivered to the normal portion (e.g., normal tissues surrounding the lesion) of the object. In order to reduce the damage to the normal portion, the collimator assembly should shield at least a portion of the leaking radiation beams within the end area (or the first region). Besides, in order to better conform to the shape of the lesion, the boundary of the treatment region should have a relatively high resolution. In the present disclosure, ways of blocking the pathways of the leaking radiation beams within the end area (or the first region) and/or improving the resolution of the treatment region may include arranging at least one jaw and/or at least one block for the MLC, operating the movement of the leaves of the MLC, etc. More detailed descriptions can be found elsewhere in the present disclosure. See, e.g., FIGS. 5A-13B and the descriptions thereof.

In some embodiments, each layer of leaves of the MLC described above may include a plurality of leaves. The number or count of the plurality of leaves in the layer of leaves may vary. For illustration purposes, the number of or count of the plurality of leaves in the layer of leaves may include 12, 24, 32, 48, 64, 80, 100, 128, etc. The plurality of leaves may be made of radiation-impermeable materials (e.g., tungsten, lead, steel, or an alloy thereof).

In some embodiments, a size of the layer of leaves may relate to one or more of a width of each leaf, a length of each leaf, a thickness of each leaf, etc. The size of the layer of leaves may be a total of sizes of the plurality of leaves. As used herein, the width of a leaf may refer to a dimension of the leaf (e.g., the y-direction illustrated in FIG. 4A) orthogonal to the direction along which a leaf moves, or referred to as a leaf moving direction (e.g., a longitudinal direction), and a radiation direction (e.g., the z-direction illustrated in FIG. 4A). The length of a leaf may refer to a dimension of the leaf that is parallel to a leaf moving direction (e.g., a longitudinal direction, the x-direction illustrated in FIG. 4A). The thickness (or height) of a leaf may refer to a dimension of the leaf along a radiation direction (e.g., the z-direction illustrated in FIG. 4A). In some embodiments, each leaf of some or all leaves in the layer of leaves may have the same width, the same length, and/or the same thickness.

In some embodiments, a shape or structure of each leaf may be non-limiting. For illustration purposes, a cross-section of each leaf may include a trapezoid, a rectangle, etc. An end of each leaf may have the shape of a rectangle, a square, an arc, etc. In some embodiments, waves or similar geometries may be arranged on leaves so that the plurality of leaves may mutually overlap as viewed from the radiation direction. For illustration purposes, the leaves may include grooves and tongues.

In some embodiments, the layer of leaves may also include a guide rail box, a plurality of driving mechanisms (e.g., a plurality of motors), and a housing (or carriage). In some embodiments, the housing may be configured to accommodate the plurality of leaves. The guide rail box may include a plurality of guide rails. Each guide rail of the plurality of guide rails may be configured to guide a movement of each leaf. The plurality of drive mechanisms may be configured to actuate the plurality of leaves to move along the plurality of guide rails. In some embodiments, at least two leaves of the plurality of leaves may be moveable parallel to each another (e.g., being movable along the x-direction illustrated in FIG. 4A).

In some embodiments, at least some of the plurality of leaves may be actuated or moved simultaneously. By simultaneously actuating and/or moving at least some of the plurality of leaves, the aperture may form. A portion of radiation beams emitted from the radiation source (e.g., the first radiation source 114) may pass through the aperture, and further travel to the treatment region (e.g., a tumor). In some embodiments, the plurality of drive mechanisms may facilitate the movement of the plurality of leaves such that the layer of leaves can transition between a first aperture shape and a second aperture shape. For illustration purposes, each leaf may be capable of transitioning from a first position to a second position (e.g., from a closed position to a target position).

The network 120 may facilitate the exchange of information and/or data. In some embodiments, one or more components of the radiation treatment system 100 (e.g., the radiation delivery device 110, the terminal 130, the processing device 140, or the storage device 150) may send information and/or data to another component(s) in the radiation treatment system 100 via the network 120. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Mere by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the radiation treatment system 100 may be connected to the network 120 to exchange data and/or information.

The terminal 130 may include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the radiation delivery device 110. In some embodiments, the terminal 130 may operate the radiation delivery device 110 via a wireless connection. In some embodiments, the terminal 130 may receive information and/or instructions inputted by a user, and send the received information and/or instructions to the radiation delivery device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the radiation delivery device 110, the terminal 130, or the storage device 150. For example, the processing device 140 may determine whether a first region exists. As used herein, the first region may form when one or more leaves of a first (or second) group of a first layer of leaves pass across a first (or second) line such that the first region is exposed to allow at least a portion of the first portion of the radiation beams to leak through.

The processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the radiation delivery device 110, the terminal 130, and/or the storage device 150 via the network 120. As another example, the processing device 140 may be directly connected to the radiation delivery device 110 (as illustrated by the dashed bidirectional arrow linking the radiation delivery device 110 and the processing device 140 in FIG. 1), the terminal 130 (as illustrated by the dashed bidirectional arrow linking the terminal 130 and the processing device 140 in FIG. 1), and/or the storage device 150, to access information and/or data. In some embodiments, the processing device 140 may be implemented on a cloud platform. Mere by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Mere by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the radiation treatment system 100 (e.g., the terminal 130, the processing device 140). One or more components of the radiation treatment system 100 may access the data or instructions stored in the storage device 150 via the network 120. In some embodiments, the storage device 150 may be directly connected to or communicate with one or more components of the radiation treatment system 100 (e.g., the terminal 130, the processing device 140). In some embodiments, the storage device 150 may be part of the processing device 140.

It should be noted that the above description is merely provided for the purposes of illustration, and not intended to limit the scope of the present disclosure. The collimator assembly described above may be configured to collimate radiation beams within a radiation area of the imaging radiation source (e.g., the second radiation source 113).

Figure 2:
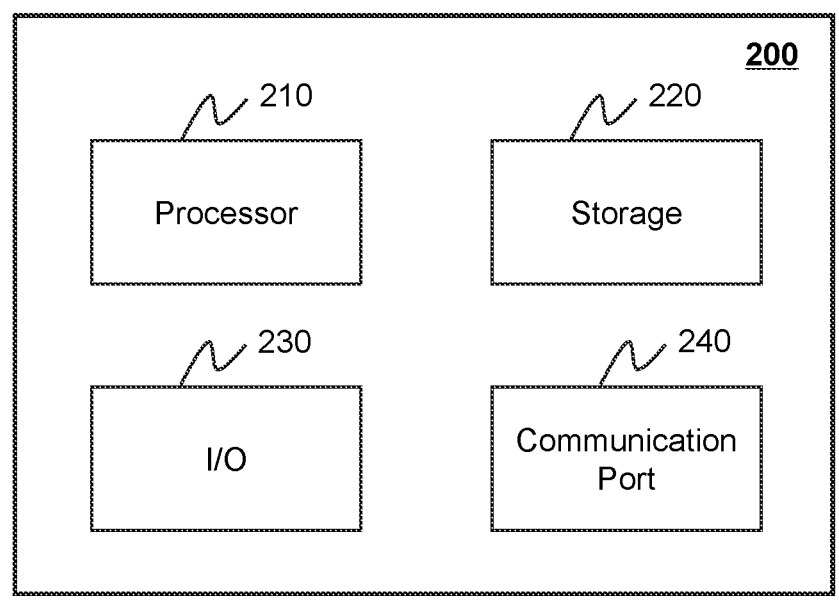
FIG. 2 is a schematic diagram illustrating exemplary hardware and/or software components of a computing device according to some embodiments of the present disclosure.

FIG. 2 is a schematic diagram illustrating exemplary hardware and/or software components of a computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the radiation delivery device 110, the terminal 130, the storage device 150, and/or any other component of the radiation treatment system 100. For example, the processing device 140 may determine whether a first region exists. As used herein, the first region may form when one or more leaves of a first (or second) group of a first layer of leaves pass across a first (or second) line such that the first region is exposed to allow at least a portion of the first portion of the radiation beams to leak through. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the radiation delivery device 110, the terminal 130, the storage device 150, or any other component of the radiation treatment system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the radiation delivery device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
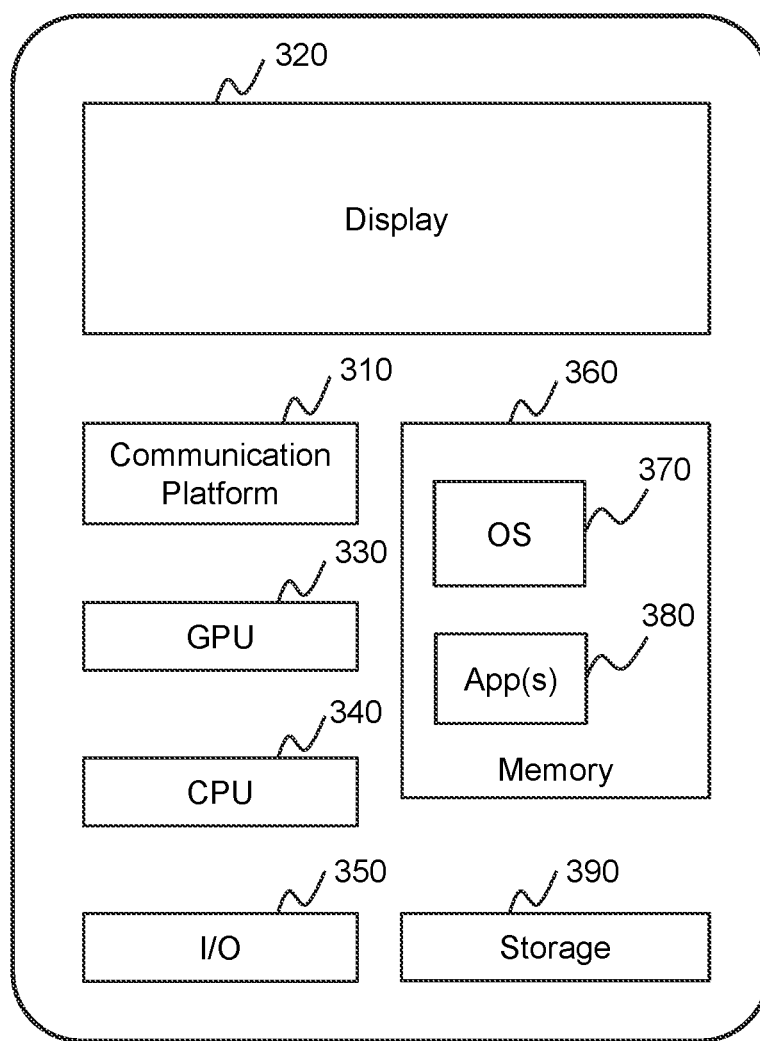
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation treatment system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to block leaking radiation beams in a region other than a treatment region and/or improve a resolution of the treatment region as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
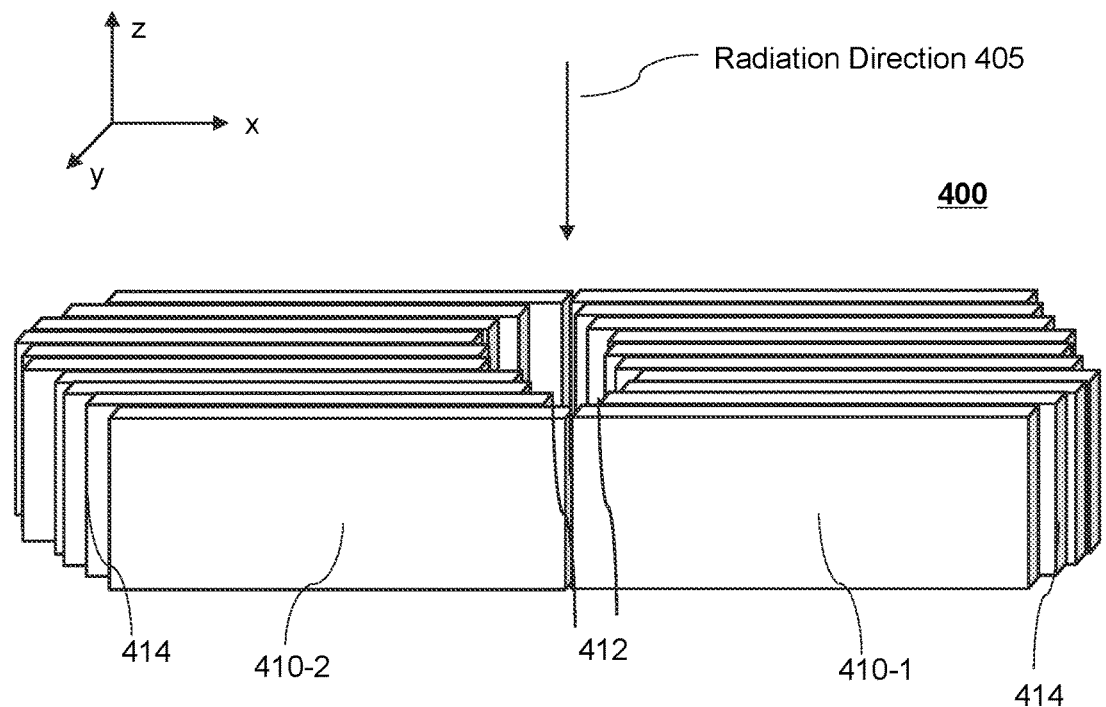
FIG. 4A is a schematic diagram illustrating an exemplary multi-leaf collimator (MLC) according to some embodiments of the present disclosure.
Figure 4B:
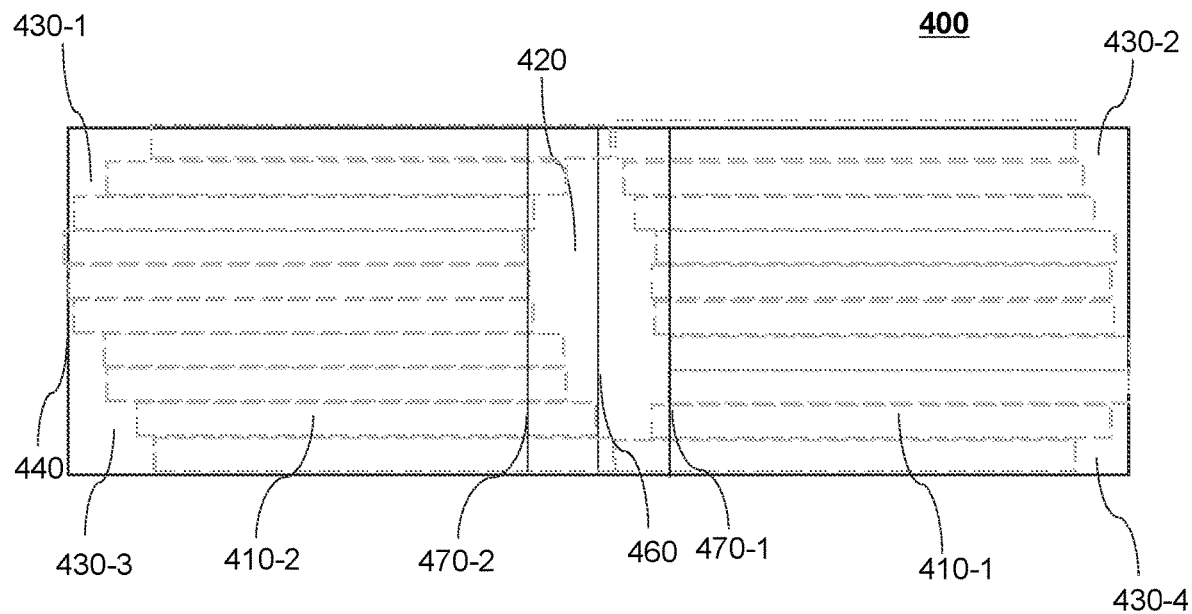
FIG. 4B is a section view illustrating an exemplary multi-leaf collimator (MLC) according to some embodiments of the present disclosure.

FIG. 4A is a schematic diagram illustrating an exemplary multi-leaf collimator (MLC) 400 according to some embodiments of the present disclosure. FIG. 4B is a section view of the MLC 400 according to some embodiments of the present disclosure.

As illustrated in FIGS. 4A-4B, the MLC 400 may have a single layer of leaves. The layer of leaves may be an example of the layer of leaves described in FIG. 1. The MLC (or the layer of leaves) may include two opposing groups of leaves, i.e., a first group of leaves 410-1 (also referred to as "leaves 410-1") and a second group of leaves 410-2 (also referred to as "leaves 410-2"). A cross-section of each leaf may be rectangular. Each leaf may include a first end (also referred to as "front end") and a second end (also referred to as "rear end") located at the ends of the leaf along the longitudinal direction of the leaf (e.g., along the x-direction). The front end 412 of a leaf may refer to the end of the leaf that faces an end of another leaf and the rear end 414 may refer to the other end of the leaf.

As illustrated in FIG. 4B, the projection of the leaves of the MLC may be represented by rectangles with dotted lines. A rectangle 440 may represent a radiation area (e.g., the maximum of the radiation area of the first radiation source 114). Similar to the collimator assembly of the radiation treatment system 100 described above, the MLC 400 may form an aperture through which a portion of radiation beams is delivered to a treatment region. A region formed by front ends of the leaves 410-1 and the leaves 410-2 may constitute the treatment region, e.g., a region 420. In some embodiments, a lesion (e.g., a tumor) of an object may be located in the region 420 for radiotherapy.

The region 420 may conform to the shape of the lesion. In order to reduce the damage of radiation beams to a normal portion (e.g., the normal tissues) of the object, pathways of radiation beams should be blocked to deliver to a region other than the region 420. However, as illustrated in FIG. 4B, except the region 420, the MLC may only shield radiation beams within a region covered by the rectangles with dotted lines, and fail to block pathways of leaking radiation beams in one or more regions, e.g., a region 430-1, a region 430-2, a region 430-3, and a region 430-4 (also collectively referred to as "end area").

As illustrated in FIG. 4B, the region 430-1 and the region 430-3 may be in the left side of the region 420 (i.e., the radiation area). The region 430-2 and the region 430-4 may be in the right side of the region 420. It should be noted the end area constituted by the region 430-1, the region 430-2, the region 430-3, and the region 430-4 may be exemplary. The end area may also include at least one region in the left side and/or at least one region in the right side (not shown in FIG. 4B). For example, the end area may include two regions in the left side. As another example, the end area may include two regions in the right side. As a further example, the end area may include a region in the right side and a region in the left side.

As illustrated in FIG. 4B, solid line 460 may represent a centerline of the rectangle 440. Each leaf may have the same length, and the length may be smaller than a half of the length of the rectangle 440. A distance between solid line 470-1 (also referred to as "first line") and a right edge of the rectangle 440 may be the same as the length of the leave. The region 430-2 and the region 430-4 may form by one or more of the leaves 410-1 passing across the solid line 470-1. Similarly, a distance between solid line 470-2 (also referred to as "second line") and a left edge of the rectangle 440 may be the same as the length of the leave. The region 430-1 and the region 430-3 may form by one or more of the leaves 410-2 passing the solid line 470-2. It should be noted that the first line and the second line may interchange. For example, solid line 470-1 may be determined as the second line, and solid line 470-2 may be determined as the first line.

Each boundary of the region 430-1, the region 430-2, the region 430-3 and the region 430-4 may be determined based on one or more second ends of the one or more leaves of the first group of leaves and a first portion of a boundary of the radiation area. As illustrated in FIG. 4B, the boundary of the region 430-1 may be determined based on second ends of three leaves in the upper side and two edges (i.e., the left edge, an upper edge) of the radiation area. The boundary of the region 430-2 may be determined based on second ends of six leaves in the upper side and two edges (i.e., the right edge, the upper edge) of the radiation area. The boundary of the region 430-3 may be determined based on second ends of five leaves in the lower side and two edges (i.e., the left edge, a lower edge) of the radiation area. The boundary of the region 430-4 may be determined based on second ends of two leaves in the lower side and two edges (i.e., the right edge, the lower edge) of the radiation area.

A resolution of the region 420 (e.g., the resolution along the z-direction illustrated in FIG. 4A) may relate to a width of each leaf that forms the boundary of the treatment region. For example, as illustrated in FIG. 4B, the boundary of the region 420 may be formed based on a plurality of steps, and each step may have the same width as each leaf (e.g., the leaf 410-1, the leaf 410-2) that forms the boundary of the region 420. For example, if the dimension of the width of the leaf is 2, the dimension of the boundary of the treatment region along the y-direction may be 2, 4, 6, . . . , 2n. As used herein, n is a positive integer. Accordingly, the dimension of the boundary of the region 420 along the y-direction may be limited by the width of the leaf, resulting in a limited resolution of the region 420.

Figure 5A:
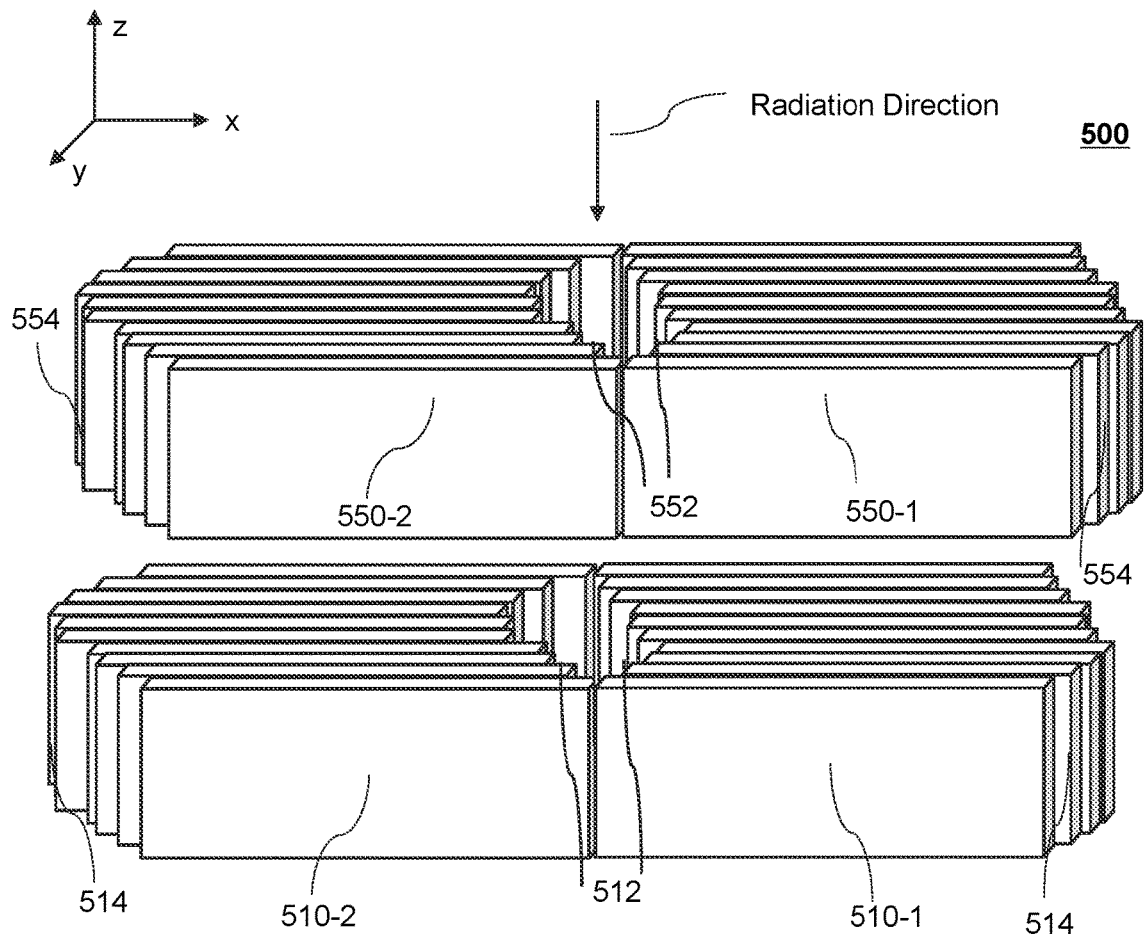
FIG. 5A is a schematic diagram illustrating an exemplary multi-leaf collimator (MLC) according to some embodiments of the present disclosure.
Figure 5B:
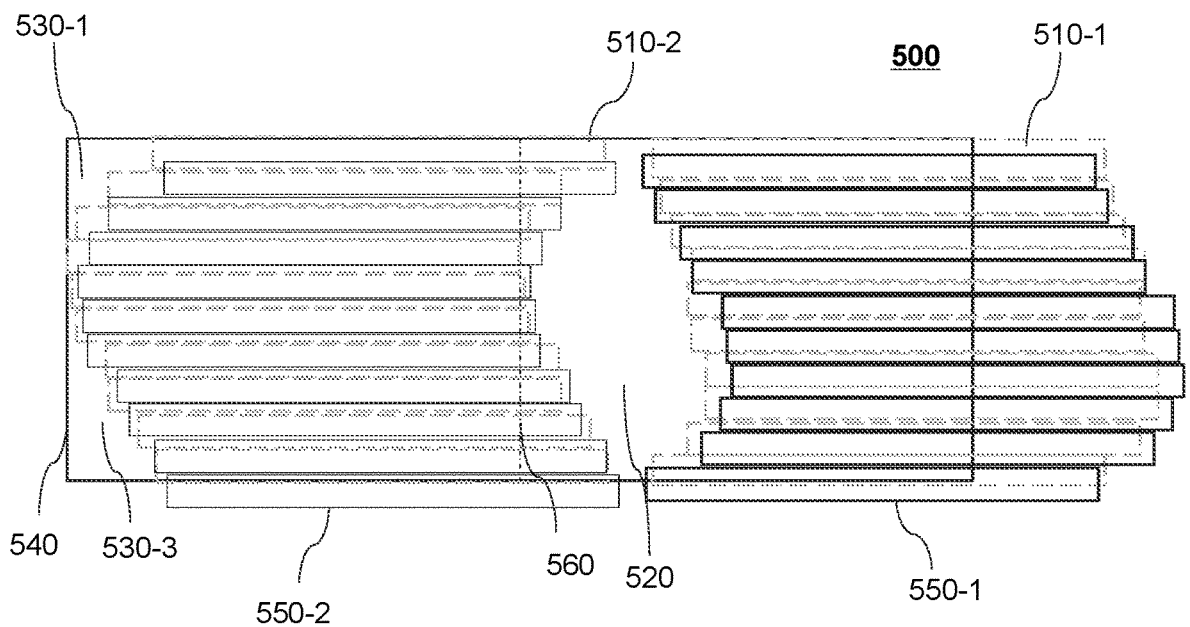
FIG. 5B is a section view illustrating an exemplary multi-leaf collimator (MLC) according to some embodiments of the present disclosure.

FIG. 5A is a schematic diagram illustrating an exemplary multi-leaf collimator (MLC) 500 according to some embodiments of the present disclosure. FIG. 5B is a section view of the MLC 500 according to some embodiments of the present disclosure.

The MLC 500 may have two layers of leaves. Each of the two layers of leaves may be similar to or the same as the layer of leaves described in FIG. 1 or FIGS. 4A-4B. As illustrated in FIGS. 5A-5B, the first layer of leaves of the MLC may include a first group of leaves 510-1 (also referred to as "leaves 510-1") and a second group of leaves 510-2 (also referred to as "leaves 510-2"). The second layer of leaves may include a first group of leaves 550-1 (also referred to as "leaves 550-1") and a second group of leaves 550-2 (also referred to as "leaves 550-2"). The leaves (i.e., the first layer of leaves, the second layer of leaves) may be similar to the leaves 410 illustrated in FIGS. 4A-4B. A cross-section of each leaf may be rectangular. Each leaf may include a first end (also referred to as "front end") and a second end (also referred to as "rear end") located at the ends of the leaf along the longitudinal direction of the leaf (e.g., along the x-direction). The front end 512 of a leaf may refer to the end of the leaf that faces an end of another leaf and the rear end 514 may refer to the other end of the leaf. The front end 552 of a leaf may refer to the end of the leaf that faces an end of another leaf and the rear end 554 may refer to the other end of the leaf.

As illustrated in FIG. 5B, the projection of the leaves of the first layer of leaves may be represented by rectangles with dotted lines. The projection of the leaves of the second layer of leaves may be represented by rectangles with solid lines. A rectangle 540 may represent a radiation area (e.g., the maximum of the radiation area of the first radiation source 114). Similar to the MLC 400 described in FIGS. 4A-4B, the MLC 500 may form an aperture through which a portion of radiation beams is delivered to a treatment region. A region formed by front ends of the leaves 510-1, the leaves 510-2, the leaves 550-1, and the leaves 550-2 may constitute the treatment region, e.g., a region 520. In some embodiments, a lesion (e.g., the tumor) of an object may be located in the region 520 for radiotherapy.

Similar to region 420, the region 520 may conform to the shape of the lesion. In order to reduce the damage of radiation beams to a normal portion (e.g., the normal tissues) of the object, pathways of radiation beams should be blocked to deliver to a region other than the region 520. However, as illustrated in FIG. 5B, except the region 520, the MLC may only shield radiation beams within a region covered by the rectangles with dotted lines and the rectangles with solid lines, and fail to block pathways of leaking radiation beams in one or more regions, e.g., a region 530-1 and a region 530-3 (also collectively referred to as "end area").

The region 530-1 and the region 530-3 may be in the left side of the region 520 (i.e., the radiation area). It should be noted that the end area constituted by the region 530-1 and the region 530-3 may be exemplary. Similar to the end area described in FIGS. 4A-4B, the end area may include at least one region in the right side of the radiation area and/or at least one region in the left side and at least one region in the right side (not shown in FIG. 4B), etc. For example, the end area may include two regions in the left side. As another example, the end area may include two regions in the right side. As a further example, the end area may include a region in the right side and a region in the left side.

As illustrated in FIG. 5B, dotted line 560 may represent a centerline of the rectangle 540. Each leaf may have the same length, and the length may be equal to a half of the length of the rectangle 540. The region 530-1 and the region 530-3 may form by one or more of the leaves 510-2 and/or one or more of the leaves 550-2 passing across the dotted line 560. Similarly, when one or more of the leaves 510-1 and/or one or more of the leaves 550-1 pass across the dotted line 560 (not shown in FIG. 5B), the MLC may fail to block leaking radiation beams in at least one region within the radiation area.

In some embodiments, in order to solve the problems (the leaking radiation beams in the end area, the limited resolution of the treatment region) described in FIG. 1 or 4A-5B, embodiments of the present disclosure may provide a collimator assembly. The collimator assembly may include an MLC having at least one layer of leaves and at least one block. The at least one block may be made of a radiation impermeable material, for example, tungsten, lead, steel, or the like, or an alloy thereof. The MLC may be situated in a first plane and the block(s) may be situated in a second plane other than the first plane. The MLC may include at least one first group of leaves and at least one second group of leaves opposing each other and being moveable along a first direction (e.g., the x-direction illustrated in FIG. 4A). The at least one block may include a block located at a position corresponding to a rear end (e.g., the rear end 414 illustrated in FIG. 4A) of the at least one first group of leaves so that the projection of the block along a second direction (e.g., the radiation direction 405 illustrated in FIG. 4A) partially overlaps the projection of the at least one first group of leaves along the second direction. As used herein, a front end of a leaf of a collimator assembly refers to the end of the leaf that participates in forming an aperture of the collimator assembly corresponding to a treatment region formed by radiation traversing the collimator assembly. As used herein, a rear end of a leaf of a collimator assembly refers to the end of the leaf that is opposite to the front end along the longitudinal direction (also referred to as "first direction") (e.g., the x-direction illustrated in FIG. 4A) of the leaf. A front end of a leaf may be located closer to the centerline of a radiation ray and/or the centerline of the radiation area/treatment region formed by radiation traversing the collimator than the rear end of the leaf.

In some embodiments, the at least one block may also include a second block located at a position corresponding to a rear end of the at least one second group of leaves so that the projection of the block along the second direction partially overlaps the projection of the at least one second group of leaves along the second direction. In some embodiments, there may be no gap between the projection of the block along the second direction and the projection of the at least one first group of leaves along the second direction and no gap between the projection of the second block along the second direction and the projection of the at least one second group of leaves along the second direction. That is, the projection of the block may at least cover rear ends of the at least one first group of leaves as illustrated in FIG. 6A; the projection of the second block may at least cover rear ends of the at least one second group of leaves as illustrated in FIG. 6B. For example, at least one leaf of the MLC may be movable to form a treatment region by blocking at least a first portion of radiation beams which the treatment radiation source (e.g., the first radiation source 114) emits. A second portion of the radiation beams may impinge on the treatment region. If the MLC fails to block pathways of leaking radiation beams within an end area other than the treatment region, the projection of the at least one block may cover the end area, thereby shielding or blocking at least a portion of the leaking radiation beams within the end area from passing through the collimator assembly. As described above, the treatment region may conform to the shape of the lesion, and the lesion (e.g., the tumor) of the object may be located in the treatment region for radiotherapy. Thus the first portion and/or the second portion of radiation beams described herein may relate to the shape of the lesion. For illustration purposes, the first portion of radiation beams may include at least a portion of radiation beams other than a portion (e.g., the second portion) of radiation beams within the treatment region.

As described above, the MLC (or the at least one layer of leaves) may be configured to form an aperture through which a portion of radiation beams is delivered to the treatment region. The treatment region may conform to the shape of the lesion, and the lesion (e.g., the tumor) of the object may be located in the treatment region for radiotherapy. The aperture (or the treatment region) may change according to the shape of the lesion of the object. In some embodiments, the aperture may change by moving at least one leaf of the first group of leaves or at least one leaf of the second group of leaves from at least one first position (e.g., forming a first aperture) to at least one second position (e.g., forming a second aperture).

Similar to the MLC described FIGS. 4A-5B, the end area may form in the radiation area when the at least one leaf of the MLC moves so that the MLC may fail to block pathways of leaking radiation beams in the end area. In some embodiments, when one or more second ends of one or more leaves of the at least one leaf are within a boundary of the radiation area, the MLC may fail to block the pathways of leaking radiation beams in the end area. Similar to the treatment region, an area of the end area may change when the at least one leaf of the first group of leaves or at least one leaf of the second group of leaves moves from the at least one first position to the at least one second position.

In some embodiments, the end area may include a first section (e.g., the region 430-2, the region 430-4 illustrated in FIG. 4B) that forms when one or more leaves of the first group of at least one of the at least one layer of leaves pass across a first line such that the first section is exposed to allow at least a portion of the first portion of the radiation beams to leak through. That is, one or more second ends (or rear ends) of the one or more leaves may be within the boundary of the radiation area. The boundary of the first section may be determined similar to or the same as the end area described FIGS. 4A-4B, the descriptions of which may be not repeated here.

In some embodiments, the first line may relate to a length of each of the first group of leaves and the length of the radiation area. For illustration purposes, the length of each of the first group of leaves may be the same, and a distance between a first edge of the radiation area and the first line may be equal to a length of each of the first group of leaves. The first edge may refer to an edge of the boundary of the radiation area that is relatively far from the second group of leaves along a longitudinal direction. In some embodiments, when the length of each of the first group of leaves may be half of the length of the radiation area, the first line may be a centerline (e.g., the dotted line 560 illustrated in FIG. 5B) of the radiation area. In some embodiments, when the length of each of the first group of leaves may be smaller than the half of the length of the radiation area, the first line may be a line (e.g. the solid line 470-1 illustrated in FIG. 4B) parallel with the centerline of the radiation area.

In some embodiments, the end area may include a second section (e.g., the region 430-1, the region 430-3 illustrated in FIG. 4B) that forms when one or more leaves of the second group of at least one of the at least one layer of leaves pass across a second line such that the second section is exposed to allow at least a portion of the first portion of the radiation beams to leak through. That is, one or more second ends (or rear ends) of the one or more leaves may be within the boundary of the radiation area. The boundary of the end area may be determined similar to or the same as the end area described FIGS. 4A-4B, the descriptions of which may be not repeated here. In some embodiments, similar to the first line, the second line may relate to a length of each of the second group of leaves. For illustration purposes, the length of each of the second group of leaves may be the same, and a distance between a second edge of the radiation area and the second line may equal to a length of each of the second group of leaves. The second edge may refer to an edge of the boundary of the radiation area that is relatively far from the first group of leaves along a longitudinal direction. In some embodiments, when the length of each of the second group of leaves may be half of the length of the radiation area, the second line may be a centerline (e.g., the dotted line 560 illustrated in FIG. 5B) of the radiation area. In some embodiments, when the length of each of the first group of leaves may be smaller than the half of the length of the radiation area, the second line may be a line (e.g. the solid line 470-2 illustrated in FIG. 4B) parallel with the centerline of the radiation area.

In some embodiments, the size (e.g., a width, a length, a thickness (or height)) of each of the at least one block may relate to a first reference distance that at least one leaf of the first group of leaves is allowed to move, a second reference distance that at least one leaf of the second group of leaves is allowed to move, a width of at least one leaf of the at least one first group of leaves, a width of at least one leaf of the at least one second group of leaves, a length of at least one leaf of the first group of leaves, or a length of at least one leaf of the second group of leaves, or the like, or any combination thereof. As used herein, the width of a block may refer to a dimension of the block (e.g., the y-direction illustrated in FIG. 4A) orthogonal to the direction along which a leaf moves, or referred to as a leaf moving direction (e.g., a longitudinal direction), and a radiation direction (e.g., the z-direction illustrated in FIG. 4A). The length of a block may refer to a dimension of the block that is parallel to a leaf moving direction (e.g., a longitudinal direction, the x-direction illustrated in FIG. 4A). The thickness (or height) of a block may refer to a dimension of the block along a radiation direction (e.g., the z-direction illustrated in FIG. 4A).

In some embodiments, the first reference distance and the second reference distance may be the same. The length of the at least one leaf of the first group of leaves and the length of at least one leaf of the second group of leaves may be the same. In some embodiments, if the length of the at least one leaf of the first group of leaves or the length of at least one leaf of the second group of leaves remains the same, the larger the first reference distance or the second reference distance is, the larger the length of each of the at least one block may be. In some embodiments, if the first reference distance or the second reference distance remains the same, the larger length of the at least one leaf of the first group of leaves or the length of at least one leaf of the second group of leaves is, the smaller the length of each of the at least one block may be.

In some embodiments, the length of the layer of leaves may be equal to the length of each leaf. The width of the layer of leaves may include a total of width of the first group of leaves or the second group of leaves. In some embodiments, the larger the width of each of the at least one layer of leaves, the larger the width of each of the at least one block may be. In some embodiments, each layer of leaves may have the same thickness. A space for holding the MLC and the at least one block may be unchangeable. The greater the number or the count of the layers of leaves in the MLC, the smaller the thickness of the at least one block may be.

In some embodiments, the size of the at least one block may also relate to a mounting mode of the at least one block. In a first mounting mode, the at least one block may be moveable with respect to the position(s) thereof along with the MLC. A region that the at least one block shields may change with the movement of the MLC. The projection of the at least one block may cover the end area during the movement of the block(s). In a second mounting mode, the at least one block may be fixed at the position(s) thereof. A region that the at least one block shields may be fixed. The projection of the at least one block may cover the end area during the movement of the MLC. In some embodiments, the projection of the at least one block may also partially overlap the MLC during the movement of the MLC. A size of the at least one block using the first mounting mode may be relatively smaller than the size of the at least one block using the second mounting mode.

In some embodiments, the at least one block may be retractable. For illustration purposes, if the end area does not exist, the at least one block may retract back. If the end area exists, the at least one block may retract out. In some embodiments, a first portion of the at least one block may be moveable or retractable. A second portion of the at least one block may be fixed.

In some embodiments, the shape and/the size of the at least one block may be determined based on empirical data or an algorithm, e.g., a Monte Carlo simulation algorithm, etc. The shape and size of the at least one block may be non-limiting if the at least one block blocks the at least a portion of leaking radiation beams within the end area. For illustration purposes, the shape of the at least one block may include rectangle, square, circle, polygon, trapezoid, etc. The size of the at least one block may be large enough to block the at least a portion of leaking radiation beams within the end area. In some embodiments, when one or more leaves of the first group of leaves pass across the first reference distance or one or more leaves of the first group of leaves passes across the second reference distance and thus forms an end area, the at least one block may block pathways of at least a portion of leaking radiation beams within the end area.

In some embodiments, the collimator assembly described above may also include at least one jaw. The at least one jaw may be made of a radiation-impermeable material. Exemplary radiation-impermeable materials may include tungsten, lead, steel, or the like, or an alloy thereof. The at least one jaw may be situated in the second plane between the at least one block. In some embodiments, a gap may exist between the projection of the at least one jaw along the second direction and the treatment region. The at least one jaw may shield or block a part of the first portion of radiation beams. In some embodiments, the projection of the at least one jaw along the second direction may partially overlap the treatment region. The at least one jaw may shield or block a part of the second portion of radiation beams. That is, the at least one jaw may form the treatment region together with the MLC. A resolution of the treatment region may be adjustable by moving the at least one jaw and at least some leaves of the MLC, alone or in combination. More detailed descriptions of adjusting the resolution of the treatment system can be found elsewhere in the present disclosure. See, e.g., FIGS. 7A-7C and the descriptions thereof.

In some embodiments, the at least one jaw and the at least one block may be situated above or upstream to the MLC along the second direction (from the treatment radiation source toward the treatment region). As used herein, component A being upstream to component B indicates that component A is closer to the treatment radiation source (e.g., the first radiation source 114) or the imaging radiation source (e.g., (e.g., the second radiation source 113) than component B. In some embodiments, the at least one jaw and the at least one block may be situated below or downstream to the MLC along the second direction. As used herein, component A being downstream to component B indicates that component B is closer to the treatment radiation source (e.g., the first radiation source 114) or the imaging radiation source (e.g., the second radiation source 113) than component A. In some embodiments, the smaller a distance from the MLC to the object is, the smaller the size of the projection of each leave of the MLC on a plane of the radiation area may be. For example, as illustrated in FIGS. 6B, the treatment region (e.g., region 620) may be part of the radiation area (e.g., region 640). Accordingly, the at least one jaw and the at least one block may be situated above or upstream to the MLC along the second direction. In some embodiments, at least one radiation non-resistant component (e.g., a circuit board) of the collimator assembly may be situated between the MLC and at least one of the at least one block or the at least one jaw.

In some embodiments of the present disclosure, in order to solve the problems (the limited resolution of the treatment region) described in FIG. 1, or 4A-5B, embodiments of the present disclosure may provide a collimator assembly. The collimator assembly may include an MLC having at least one layer of leaves and at least one jaw. The MLC may be situated in a first plane and the at least one jaw may be situated in a second plane other than the first plane. Similar to the collimator assembly described above, one or more leaves of the MLC may be moveable to form a treatment region. The projection of the at least one jaw may partially overlap the treatment region. Thus the at least one jaw may shape the treatment region together with the MLC. In some embodiments, a resolution of the treatment region may be adjustable by moving the at least one jaw. More detailed descriptions of the collimator assembly can be found elsewhere in the present disclosure. See, e.g., FIGS. 8A-8B and the descriptions thereof.

In some embodiments of the present disclosure, in order to solve the problems (the leaking radiation beams in the end area, the limited resolution of the treatment region) described in FIG. 1 or 4A-5B, embodiments of the present disclosure may provide a method for operating a collimator assembly. The collimator assembly may include an MLC having a first layer of leaves and a second layer and/or at least one block. If the first layer of leaves and the at least one block fails to block pathways of leaking radiation beams within an end area (or a first region) associated with the collimator assembly, a portion of the second layer of leaves may be operated to block the pathways of leaking radiation beams. A portion of leaves other than the first layer of leaves and the portion of second layer of leaves of the MLC may be operated to form a treatment region associated with the first layer of leaves. More detailed descriptions of operating the collimator assembly can be found elsewhere in the present disclosure. See, e.g., FIGS. 9-13 and the descriptions thereof.

FIG. 6A is a schematic diagram illustrating a collimator assembly 600 according to some embodiments of the present disclosure. FIG. 6B is a section view illustrating the collimator assembly 600 according to some embodiments of the present disclosure.

The collimator assembly 600 may include an MLC having a single layer of leaves, a first block 630-1, and a second block 630-2. The MLC (or the layer of leaves) may include a first group of leaves 610-1 (also referred to as "leaves 610-1") and a second group of leaves 610-2 (also referred to as "leaves 610-2"). The two blocks (i.e., the first block 630-1, the second block 630-2) may be situated in a plane above the MLC.

As illustrated in FIG. 6B, a rectangle 640 may represent a radiation area (a maximum of the radiation area of the first radiation source 114). A region formed by front ends of the leaves 610-1, the leaves 610-2 may constitute a treatment region associated with the collimator assembly 600, e.g., a region 620. The projection of the MLC and the two blocks may cover a region other than the treatment region, that is, radiation beams within the region are shielded by the MLC and the two blocks.

Figure 7A:
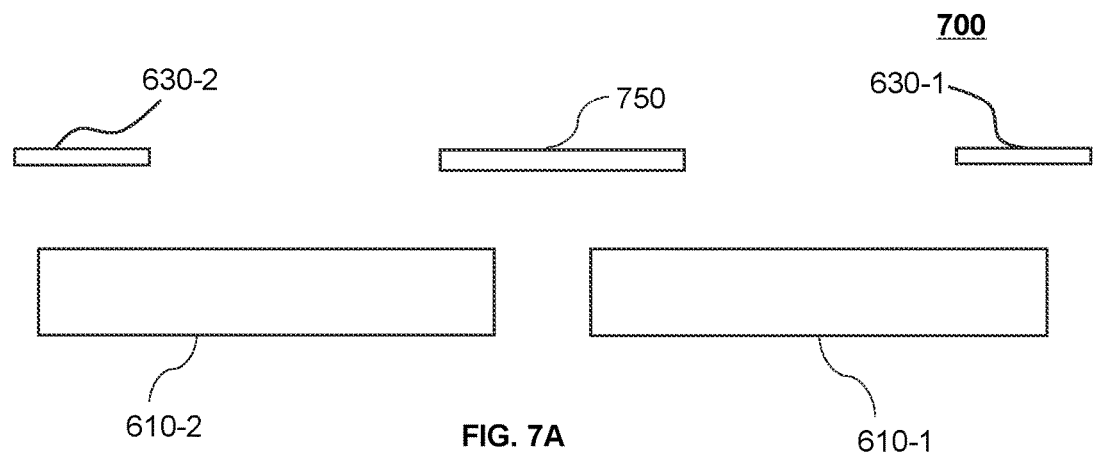
FIGS. 7A-7C are section views illustrating an exemplary collimator assembly according to some embodiments of the present disclosure.
Figure 7B:
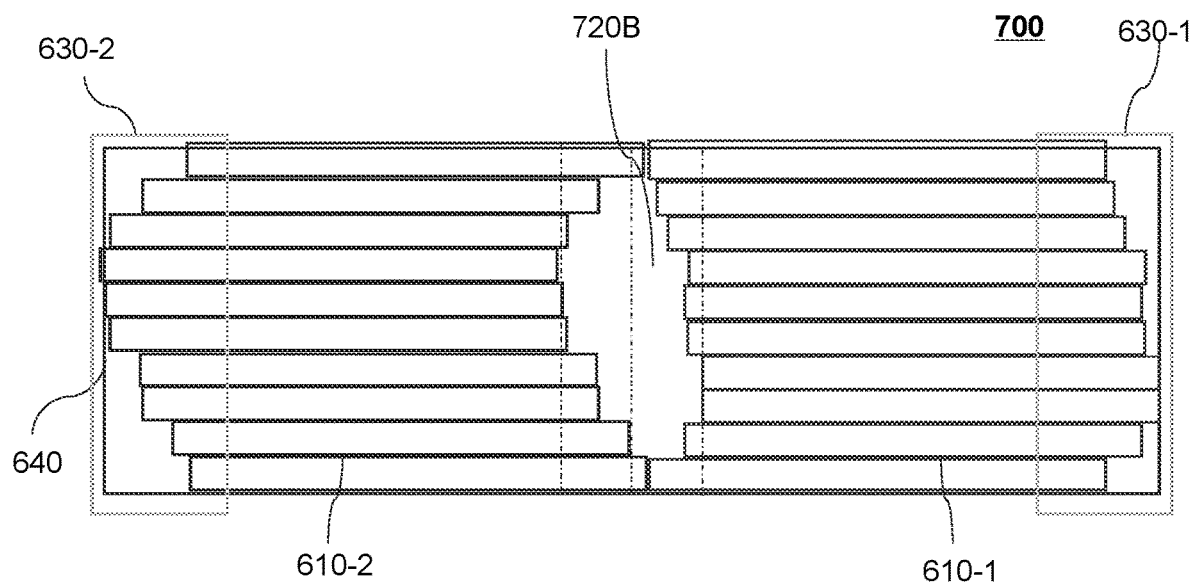
Figure 7C:
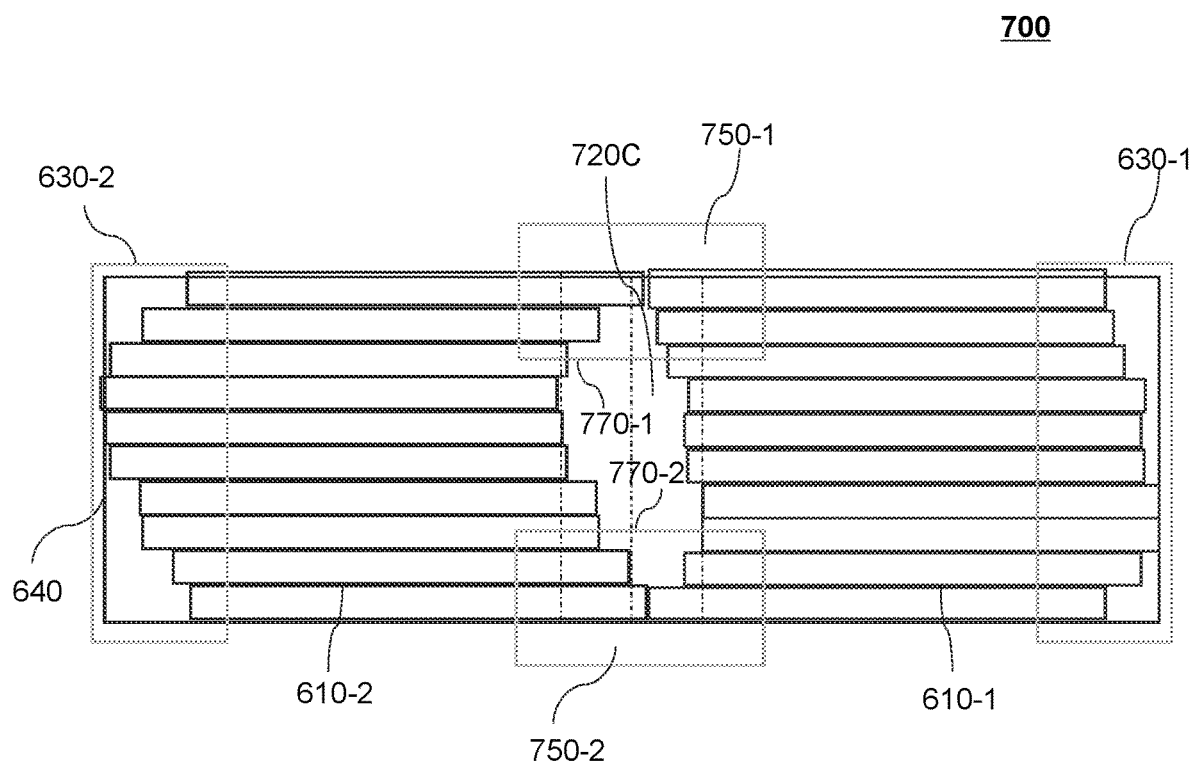

FIGS. 7A-7C are section views illustrating a collimator assembly 700 according to some embodiments of the present disclosure. The collimator assembly 700 may be similar to the collimator assembly 600 except that the collimator assembly 700 further includes a first jaw 750-1 and a second jaw 750-2. The two jaws (i.e., the first jaw 750-1, the second jaw 750-2) may be situated in a same plane as and between the two blocks (i.e., the first block 630-1, the second block 630-2).

In some embodiments, a gap may exist between the projection of the two jaws and a treatment region associated with the collimator assembly 700. As illustrated in FIG. 7B, a region formed by front ends of the leaves 610-1 and the leaves 610-2 may constitute the treatment region, e.g., a region 720B. In some embodiments, the projection of the two jaws may partially overlap the treatment region associated with the collimator assembly 700, i.e., the two jaws form the treatment region together with the MLC. As illustrated in FIG. 7C, a region formed by front ends of the leaves 610-1, the leaves 610-2, and edges 770-1 and 770-2 of the two jaws may constitute the treatment region, e.g., a region 720C. The projection of the MLC, the two blocks, and the two jaws may cover a region other than the treatment region, that is, radiation beams within the region are shielded by the MLC, the two blocks, and the two jaw.

As illustrated in FIG. 7C, the resolution of the region 720C may be adjusted by moving the two jaws. For example, if the dimension of the width of the leaf is 2, the dimension of the boundary of the treatment region along the y-direction may be 2, 4, 6, . . . , 2n without the two jaws. By moving the two jaws to allow at least one of the two edges 770-1 and 770-2 located in a step formed by a leaf of the MLC, the dimension of the boundary of the treatment region along the z-direction may be any values. Accordingly, the resolution of the treatment region 720C can be improved compared to that of the region 720B.

It should be noted that the above description is merely provided for the purposes of illustration, and not intended to limit the scope of the present disclosure. For example, the collimator assembly 700 may include an MLC having multiple layers of leaves, two jaws, and two blocks.

Figure 8A:
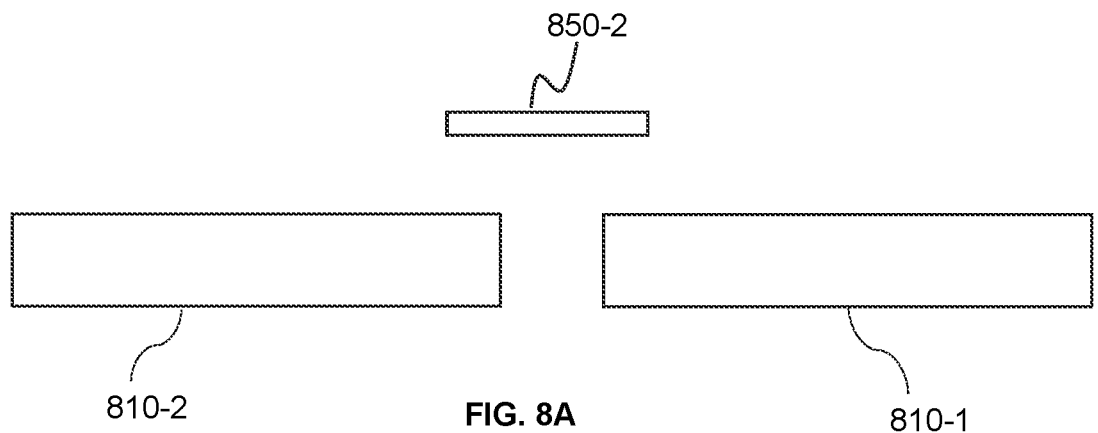
FIGS. 8A-8B are section views illustrating an exemplary collimator assembly according to some embodiments of the present disclosure.
Figure 8B:
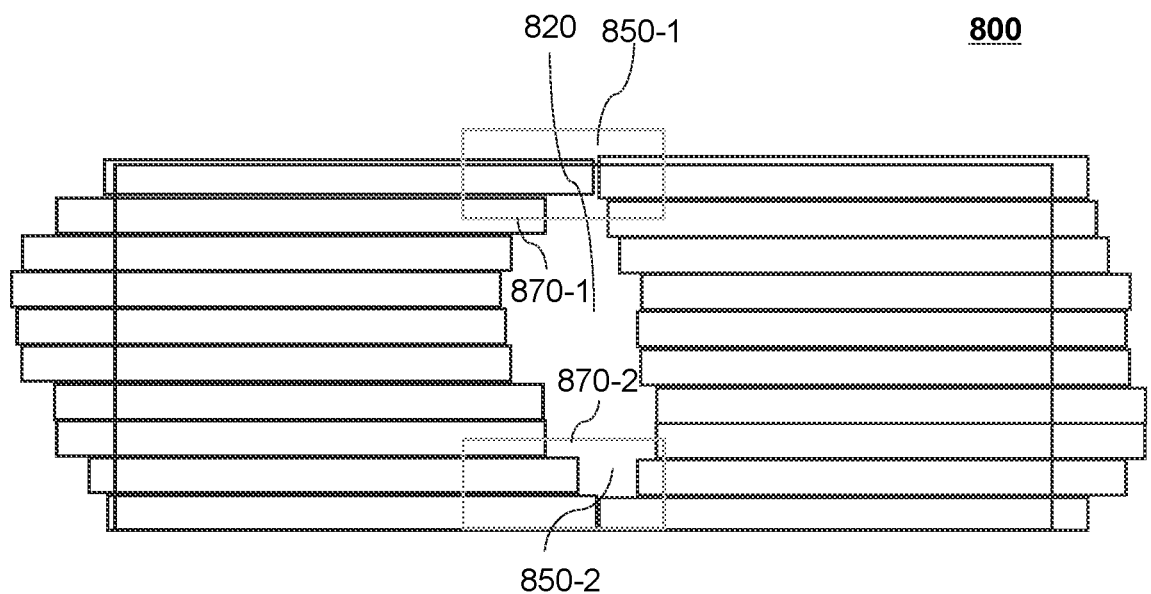

FIGS. 8A-8B are section views illustrating a collimator assembly 800 according to some embodiments of the present disclosure.

The collimator assembly 800 may include an MLC having a single layer of leaves, a first jaw 850-1, and a second jaw 850-2. The MLC (or the layer of leaves) may include a first group of leaves 810-1 (also referred to as "leaves 810-1") and a second group of leaves 810-2 (also referred to as leaves 810-2"). The leaves 810-1 and leaves 810-2 may be similar to the leaves 410-1 (or 610-1) and leaves 410-2 (or 610-2), the descriptions of which may be not repeated here. As illustrated in FIG. 8A, the two jaws (i.e., the first jaw 850-1, the second jaw 850-2) may be situated above the MLC.

The two jaws may form a treatment region associated with the collimator assembly 800 together with the MLC. A region formed by front ends of the leaves 810-1 and the leaves 810-2 and two edges 870-1 and 870-2 of the two jaws may constitute the treatment region, e.g., a region 820. In some embodiments, a resolution of the region 820 may be adjusted by moving the two jaws. More detailed descriptions of adjusting the resolution of the treatment region by moving the two jaws can be found elsewhere in the present disclosure. See, e.g., FIGS. 7A-7C and the descriptions thereof.

It should be noted that the above description is merely provided for the purposes of illustration, and not intended to limit the scope of the present disclosure. For example, the collimator assembly 800 may include an MLC having multiple layers of leaves and two jaws.

Figure 9:
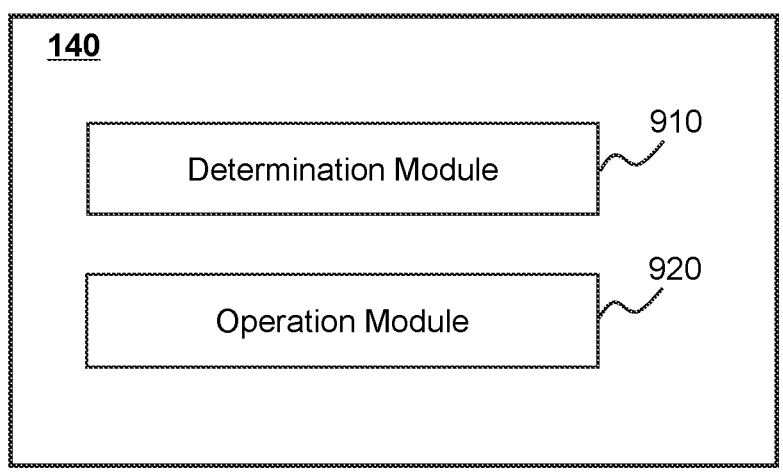
FIG. 9 is a block diagram illustrating an exemplary processing device according to some embodiments of the present disclosure.

FIG. 9 is a block diagram illustrating an exemplary processing device 140 according to some embodiments of the present disclosure. The processing device 140 may be implemented on the computing device 200 (e.g., the processor 210) illustrated in FIG. 2 or the CPU 340 illustrated in FIG. 3. The processing device 140 may include a determination module 910 and an operation module 920.

The processing device 140 may implement a process for operating a collimator assembly. The collimator assembly may include a multi-leaf collimator (MLC) at least having a first layer of leaves and a second layer of leaves. At least a portion of leaves of the MLC may be moveable to form a treatment region by blocking pathways of a first portion of radiation beams within a radiation area associated with the collimator assembly. A second portion of the radiation beams may impinge on a treatment region. The first (or second) portion of the radiation beams may be similar to the first (or second) portion of the radiation beams illustrated in FIGS. 5A-5B, the descriptions of which may be not repeated here.

The determination module 910 may be configured to determine whether a first region exists. As described above, the first region may form when one or more leaves of the first (or second) group of the first layer of leaves pass across a first (or second) line such that the first region is exposed to allow at least a portion of the first portion of the radiation beams to leak through. More detailed descriptions of the first (or second) line can be found elsewhere in the present disclosure. See, e.g., FIGS. 4A-6B. If the collimator assembly only includes the MLC, in response to determining that the first region exists, the operation module 920 may cause one or more leaves of a second layer of leaves of the MLC to move to block pathways of at least a portion of leaking radiation beams within the first region. In response to determining that the first region does not exist, the operation module 920 may cause the second layer of leaves to move to block a part of the second portion of the radiation beams. In some embodiments, the operation module 920 may cause one or more leaves of the second layer of leaves to move to block the part of the second portion of the radiation beams. In some embodiments, the operation module 920 may cause all leaves of the second layer of leaves to move to block the part of the second portion of the radiation beams. For example, the operation module 920 may cause the one or more leaves or all leaves of the second layer of leaves to move along with the first layer of leaves.

In some embodiments, the collimator assembly may also include at least one block similar to or the same as the at least one block described in FIGS. 5A-7C. If the at least one block is fixed, in response to determining that the first region exists, the operation module 920 may cause one or more leaves or all leaves of the second layer of leaves to move to block a part of the second portion of the radiation beams. In some embodiments, the operation module 920 may cause the one or more leaves or all leaves of the second layer of leaves to move along with the first layer of leaves. If the at least one block is moveable, in response to determining that the first region exists, the operation module 920 may determine whether the at least one block is able to move. In response to determining that the at least one block is able to move, the operation module 920 may cause the at least one block to block the pathways of the at least a portion of the leaking radiation beams in the first region, and cause one or more leaves or all leaves of the second layer of leaves to move to block a part of the second portion of the radiation beams. In response to determining that the at least one block is unable to move, the operation module 920 may cause one or more leaves of the second layer of leaves to shield the at least a portion of the leaking radiation beams in the first region.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

Figure 10:
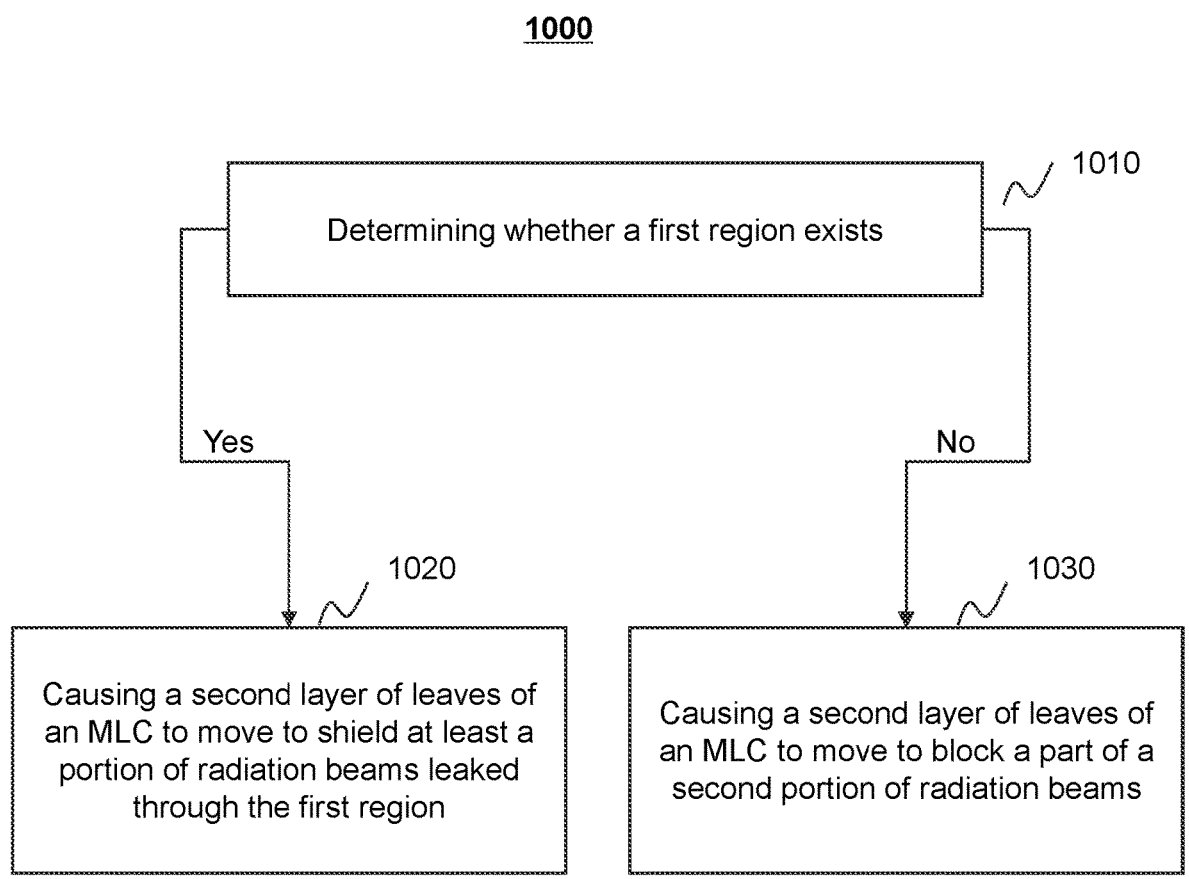
FIG. 10 is a flowchart illustrating an exemplary process for operating a collimator assembly according to some embodiments of the present disclosure.

FIG. 10 is a flowchart illustrating an exemplary process 1000 for operating a collimator assembly according to some embodiments of the present disclosure. The process 1000 may be implemented in the radiation treatment system 100 illustrated in FIG. 1. For example, the process 1000 may be stored in the storage device 150 and/or the storage 220 in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 9). The operations of the illustrated process presented below are intended to be illustrative. In some embodiments, the process 1000 may be accomplished with one or more additional operations not described, and/or without one or more of the operations discussed. Additionally, the order in which the operations of the process 1000 illustrated in FIG. 10 and described below is not intended to be limiting.

The collimator assembly may include an MLC at least having a first layer of leaves and a second layer of leaves. At least a portion of leaves of the MLC may be moveable to form a treatment region by blocking pathways of a first portion of radiation beams within a radiation area associated with the collimator assembly. A second portion of the radiation beams may impinge on a treatment region. The first (or second) portion of the radiation beams may be similar to the first (or second) portion of the radiation beams illustrated in FIG. 5, the descriptions of which may be not repeated here.

In 1010, the processing device 140 (e.g., the determination module 910) may determine whether a first region exists. As described above, the first region may form when one or more leaves of the first (or second) group of the first layer of leaves pass across a first line (or second) such that the first region is exposed to allow at least a portion of the first portion of the radiation beams to leak through. More detailed descriptions of the first (or second) line can be found elsewhere in the present disclosure. See, e.g., FIGS. 4A-6B.

The processing device 140 (e.g., the operation module 920) may cause a second layer of leaves of the MLC to operate based on a determination result in 1010. For illustration purposes, the MLC may include the first layer of leaves and the second layer of leaves. In response to determining that the first region exists, the processing device 140 may cause the second layer of leaves of the MLC to move to block pathways of at least a portion of leaking radiation beams within the first region in 1020, which may reduce the damage of the leaking radiation beams within the first region to the normal tissues of the object. In some embodiments, the processing device 140 may transmit an instruction for blocking the pathways of the at least a portion of the leaking radiation beams within the first region to the second layer of leaves. The processing device 140 may move the second layer of leaves to a position to block the pathways of the at least a portion of the leaking radiation beams.

In some embodiments, the processing device 140 may cause a first portion of the second layer of leaves to block the pathways of the at least a portion of the leaking radiation beams within the first region. Specifically, the processing device 140 may cause a second portion of the second layer of leaves to block a part of the second portion of the radiation beams. In some embodiments, the second portion of the second layer of leaves may also block at least a portion of radiation beams in a sub region within the first region. Further, the processing device 140 may cause the first portion of the second layer of leaves to shield the at least a portion of leaking radiation beams within a region of the first region other than the sub region.

Figure 11A:
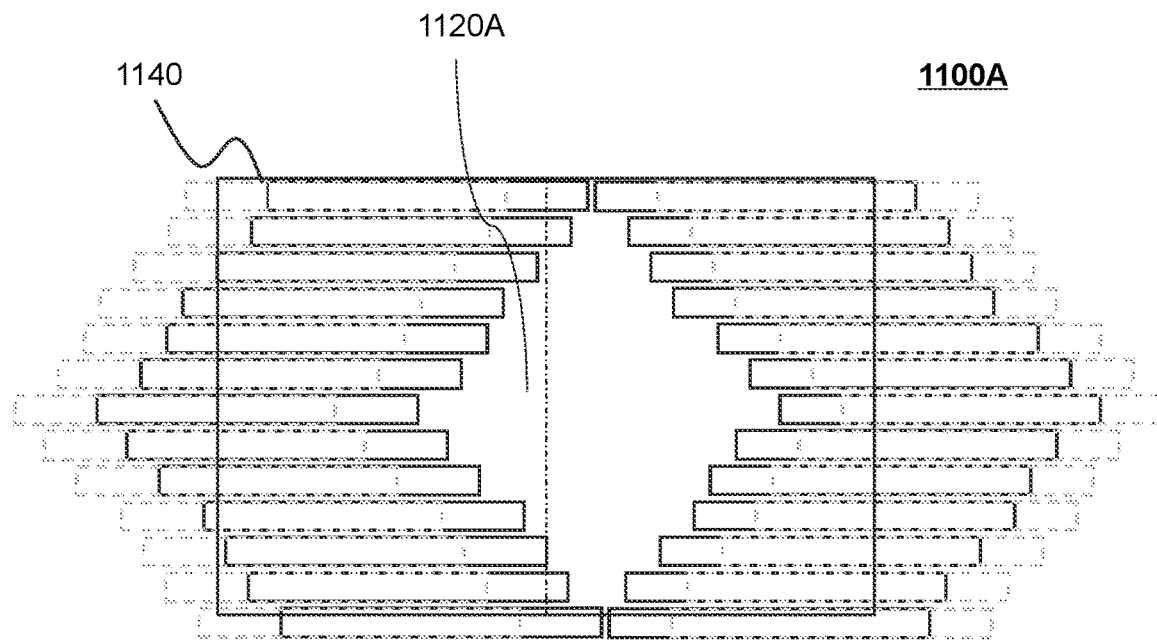
FIGS. 11A-11C are section views for operating exemplary collimator assemblies according to some embodiments of the present disclosure.
Figure 11B:
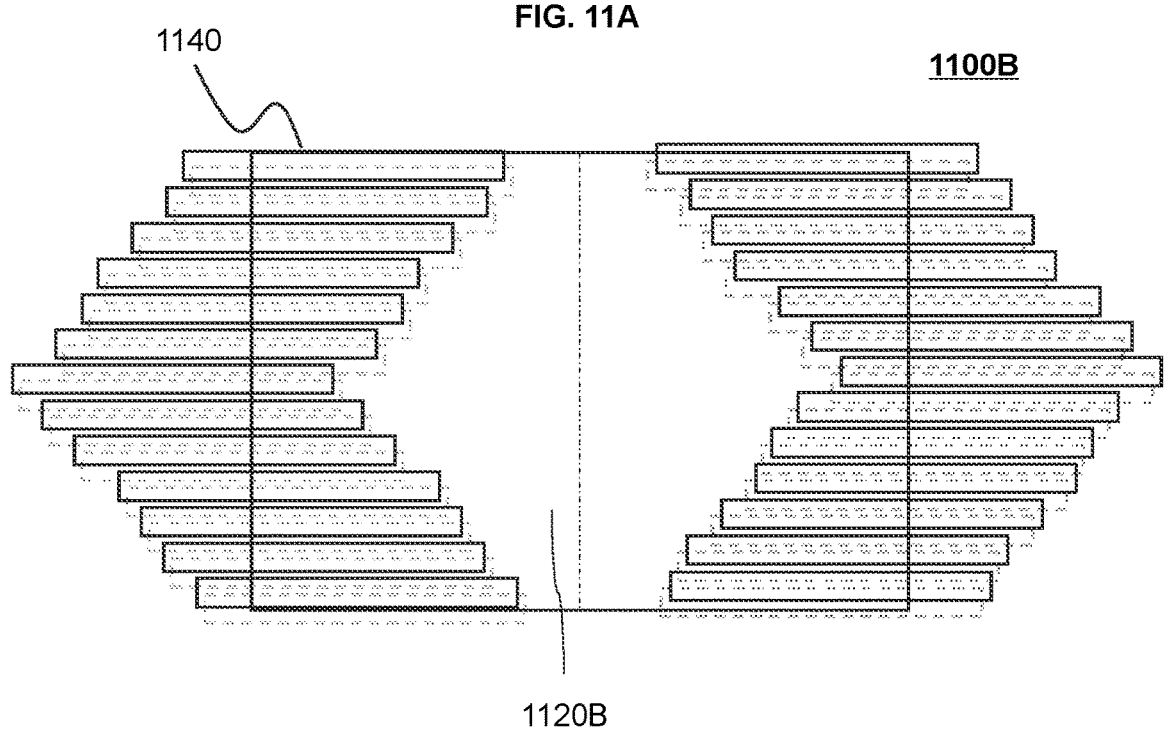
Figure 11C:
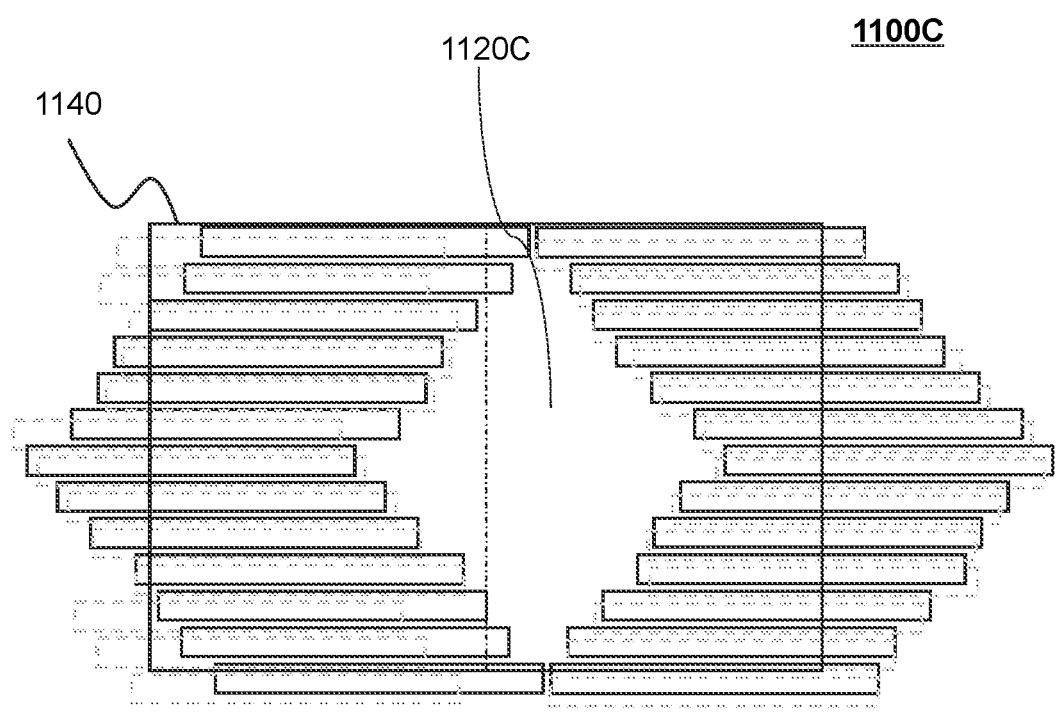

The second portion of the second layer of leaves may form the treatment region with the first layer of leaves. In some embodiments, the second portion of the second layer of leaves may move along with the first layer of leaves. A boundary of the treatment region may be formed based on a plurality of steps (e.g., as illustrated in FIG. 11C), and at least one width of the plurality of steps may be smaller than the width of each leaf. Thus the resolution (or the fine degree) of the boundary of the treatment region may be improved compared to a boundary of a treatment region formed by the first layer of leaves (e.g., as illustrated in FIG. 11A).

In response to determining that the first region does not exist, the processing device 140 (e.g., the operation module 920) may cause at least a part of the second layer of leaves to move to block a part of the second portion of radiation beams 1030. In some embodiments, the processing device 140 may cause one or more leaves of the second layer of leaves to move to block the part of the second portion of the radiation beams. In some embodiments, the processing device 140 may cause all leaves of the second layer of leaves to move to block the part of the second portion of the radiation beams. In some embodiments, the processing device 140 may transmit an instruction for moving to block the part of the second portion of radiation beams to the second layer of leaves. A boundary of the treatment region may be formed based on a plurality of steps (e.g., as illustrated in FIG. 11B), and at least one width of the plurality of steps may be smaller than the width of each leaf. Thus the resolution (or the fine degree) of the boundary of the treatment region may be improved compared to a boundary of a treatment region formed by the first layer of leaves (e.g., as illustrated in FIG. 11A).

In some embodiments, the MLC may include more than the two layers of leaves. In response to determining that the first region exists, the processing device 140 may cause at least a portion of one or more layers of leaves other than the first layer of leaves and the second layer of leaves to move to block a part of the second portion of the radiation beams. In some embodiments, the at least a portion of the one or more layers of leaves other than the first layer of leaves and the second layer of leaves may also block at least a portion of radiation beams in a first sub region within the first region. Further, the processing device 140 may cause the second layer of leaves to shield the at least a portion of leaking radiation beams within a region of the first region other than the first sub region.

Similarly, in some embodiments, the processing device 140 may cause a first portion of the second layer of leaves to shield the at least a portion of leaking radiation beams within the first region. Specifically, the processing device 140 may cause a second portion of the second layer of leaves to block a part of the second portion of the radiation beams. In some embodiments, the second portion of the second layer of leaves may also block at least a portion of radiation beams in a second sub region within the first region. Further, the processing device 140 may cause the first portion of the second layer of leaves to shield the at least a portion of leaking radiation beams within a region of the first region other than the first sub region and the second sub region.

In response to determining that the first region does not exist, the processing device 140 (e.g., the operation module 920) may cause at least a portion of the one or more layers of leaves and the second layer of leaves to move to block a part of the second portion of radiation beams. In some embodiments, the at least a portion of the one or more layer of leaves and the second layer of leaves may move along with the first layer of leaves. In some embodiments, the processing device 140 may transmit an instruction for moving to block a part of the second portion of radiation beams to the layer of leaves other than the first layer of leaves.

By providing the method described above, the MLC may simultaneously form the treatment region and block at least a portion of the leaking radiation beams delivered to the normal portion of the object other than the lesion. In some cases, a boundary of the treatment region may be formed based on a plurality of steps, and at least one width of the plurality of steps may be smaller than the width of each leaf. Thus the resolution (or the fine degree) of the boundary of the treatment region may be improved compared to a boundary of a treatment region formed by the first layer of leaves.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIGS. 11A-11C are section views for operating collimator assemblies 1100A-1100C according to some embodiments of the present disclosure. The collimator assemblies 1100A-1100C may be examples of the collimator assembly illustrated in FIG. 10.

The collimator assembly 1100A, 1100B or 1100C may have a first layer of leaves and a second layer of leaves. As illustrated in FIGS. 11A-11C, rectangles with solid lines may represent leaves in the first layer of leaves. Rectangles with dotted lines may represent leaves in the second layer of leaves. A rectangle 1140 may represent a radiation area (e.g., the maximum of the radiation area of the first radiation source 114). As illustrated in FIG. 11A, the first layer of leaves may fail to block pathways of leaking radiation beams within a first region, and the second layer of leaves may be moved to block pathways of at least a portion of the leaking radiation beams within the first region. As illustrated in FIG. 11B, the first layer of leaves may block the pathways of leaking radiation beams within the first region, the second layer of leaves may move along with the first layer of leaves. As illustrated in FIG. 11C, the first layer of leaves may fail to block pathways of leaking radiation beams within a first region. A portion of the second layer of leaves may be moved to block pathways of the leaking radiation beams within the first region. A second portion of the second layer of leaves may form the treatment region with the first layer of leaves.

As illustrated in FIG. 11A, a boundary of the treatment region 1120A may be formed based on a plurality of steps, and a width of each step may be the same as a width of each leaf of the first layer of leaves. As illustrated in FIG. 11B, a boundary of the treatment region 1120B may be formed based on a plurality of steps, and a width of each step may be smaller than or equal to the width of each leaf of the first layer of leaves or the second layer of leaves. As illustrated in FIG. 11C, a boundary of the treatment region 1120C may be formed based on a plurality of steps, and a width of each step may be smaller than or equal to the width of each leaf of the first layer of leaves or the second layer of leaves. As described in FIG. 1, the resolution may be used to represent a fine degree of a boundary of a treatment region (or aperture). The higher the resolution is, the finer the boundary of the treatment region may be. A resolution of the treatment region 1120B may be higher than a resolution of the treatment region 1120A. A resolution of the treatment region 1120C may be higher than a resolution of the treatment region 1120A.

In some embodiments, the collimator assembly 1100A, 1100B, or 1100C may also include at least one jaw (not shown in FIGS. 11A-11C). For example, the at least one jaw may also block a part of radiation beams of the region 1120A, the region 1120B, or the region 1120C, i.e., the at least one jaw may shape the target region together with the MLC.

Figure 12:
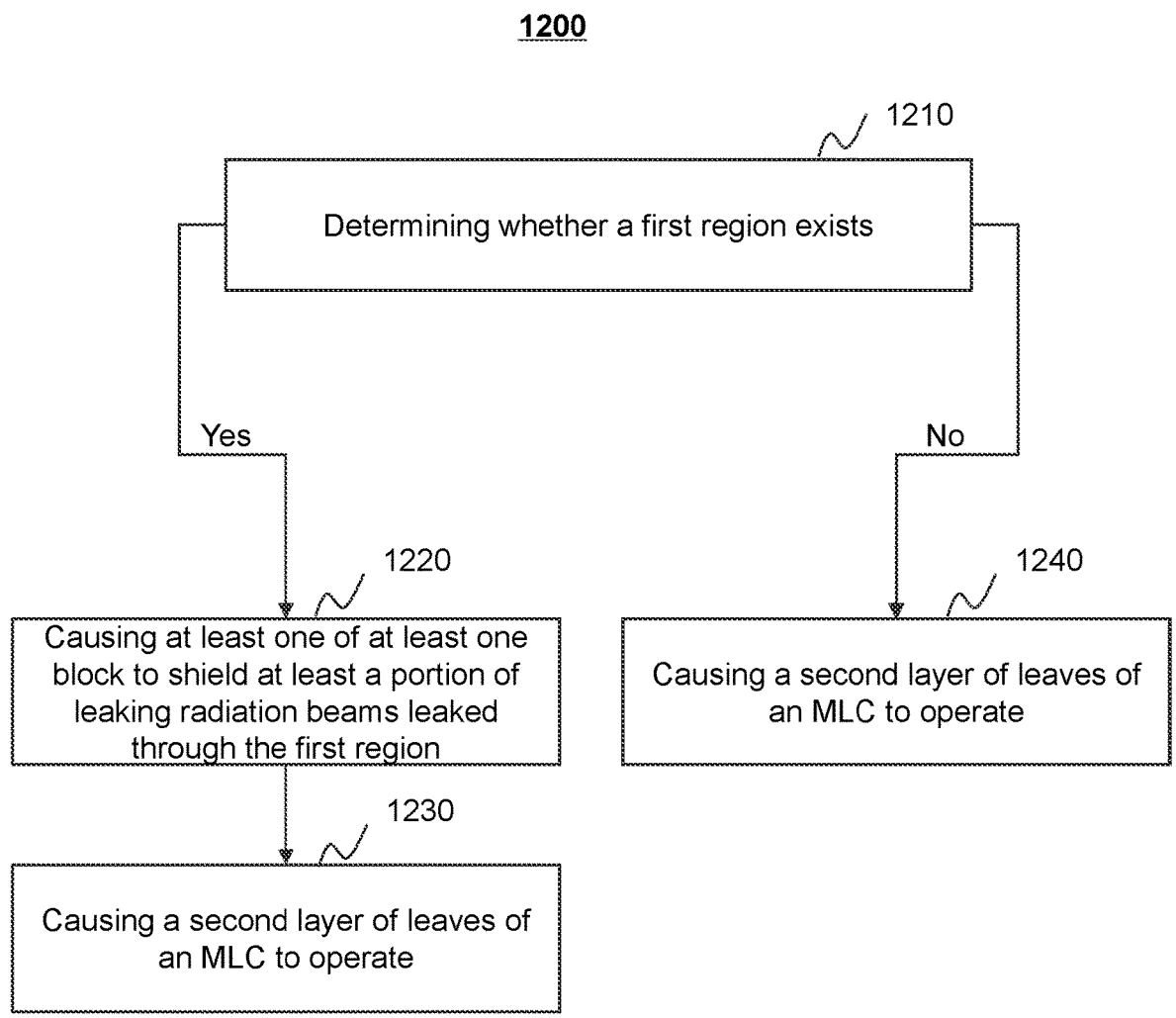
FIG. 12 is a flowchart illustrating an exemplary process for operating a collimator assembly according to some embodiments of the present disclosure.

FIG. 12 is a flowchart illustrating an exemplary process 1200 for operating a collimator assembly according to some embodiments of the present disclosure. The process 1200 may be implemented in the radiation treatment system 100 illustrated in FIG. 1. For example, the process 1200 may be stored in the storage device 150 and/or the storage 220 in the form of instructions (e.g., an application), and invoked and/or executed by the processing device 140 (e.g., the processor 210 illustrated in FIG. 2, the CPU 340 illustrated in FIG. 3, or one or more modules in the processing device 140 illustrated in FIG. 9). The operations of the illustrated process presented below are intended to be illustrative. In some embodiments, the process 1200 may be accomplished with one or more additional operations not described, and/or without one or more of the operations discussed. Additionally, the order in which the operations of the process 1200 illustrated in FIG. 12 and described below is not intended to be limiting.

The collimator assembly may at least include an MLC having at least two layers of leaves and at least one block. In some embodiments, the at least two layers of leaves may be arranged stacked one above another. For example, the at least two layers of leaves may be arranged in parallel and have an offset such that each leaf in first layer of leaves may be offset from a leaf in second layer of leaves, e.g., in the longitudinal direction. At least a portion of leaves of the MLC may be movable to form a treatment region by blocking pathways of a first portion of radiation beams within a radiation area associated with the collimator assembly. A second portion of the radiation beams the MLC may impinge on the treatment region. The first (or second) portion of the radiation beams may be similar to the first (or second) portion of the radiation beams illustrated in FIG. 5, the descriptions of which may be not repeated here.

The MLC may be situated in a first plane. The at least one block may be situated in a second plane different from the first plane. The at least one block may be configured to block pathways of at least a portion of leaking radiation beams within a first region other than the treatment region. A first layer of leaves of the MLC may fail to block leaking radiation beams within the first region. In some embodiments, the projection of the at least one block along a second direction (e.g., the radiation direction 405 illustrated in FIG. 4A) may cover the first region thereby blocking the at least a portion of the leaking radiation beams within the first region. The at least one block may be similar to or the same as the at least one block described in FIGS. 5A-7C, the descriptions of which may be not repeated here.

In 1210, the processing device 140 (e.g., the determination module 910) may determine whether the first region exists. As described above, the first region may form when one or more leaves of the first (or second) group of the first layer of leaves pass across a first (or second) line such that the first region is exposed to allow at least a portion of the first portion of the radiation beams to leak through. More detailed descriptions of the first (or second) line can be found elsewhere in the present disclosure. See, e.g., FIGS. 4A-6B and the descriptions thereof.

In response to determining that the first region exists, the processing device 140 (e.g., the operation module 920) may cause at least one of the at least one block or a second layer of leaves of the MLC to operate. In some embodiments, if the at least one block is fixed, the projection of the at least one block along the second direction may cover the first region. The processing device 140 may operate one or more layers of leaves other than the first layer of leaves of the MLC to operate. In some embodiments, the processing device 140 may operate at least a portion of the one or more layer of leaves other than the first layer of leaves to block a part of the second portion of the radiation beams. For example, the at least a portion of the one or more layers of leaves other than the first layer of leaves may move along with the first layer of leaves.

In some embodiments, if the at least one block is moveable, the processing device 140 may first determine whether the at least one block is able to move. In response to determining that the at least one block is able to move, the processing device 140 may cause the at least one block to move to shield the at least a portion of radiation beams leaked through the first region in 1220. The processing device 140 may operate the one or more layers of leaves (e.g., the second layer of leaves) other than the first layer of leaves of the MLC to operate in 1230. In some embodiments, the processing device 140 may operate at least a portion of the one or more layers of leaves other than the first layer of leaves to block a part of the second portion of the radiation beams. For example, the at least a portion of the one or more layers of leaves other than the first layer of leaves may move along with the first layer of leaves. In response to determining that the at least one block is unable to move, the processing device 140 may operate the collimator assembly similar to the process 1000, the descriptions of which may be not repeated here.

In response to determining that the first region does not exist, the processing device 140 may cause the one or more layers of leaves (e.g., the second layer of leaves) other than the first layer of leaves to move to form the treatment region in 1240. In some embodiments, the processing device 140 may operate at least a portion of the one or more layers of leaves other than the first layer of leaves to block a part of the second portion of the radiation beams. For example, the at least a portion of the one or more layers of leaves other than the first layer of leaves may move along with the first layer of leaves.

By providing the method described above, when the at least one block fails to block the at least a portion of leaking radiation beams, the MLC may be operated to block the at least a portion of leaking radiation beams, thereby ensuring the leaking radiation beams not to be delivered to the normal portion of the object other than the lesion. In some cases, a boundary of the treatment region may be formed based on a plurality of steps. At least one width of the plurality of steps may be smaller than the width of each leaf. Thus the resolution (or the fine degree) of the boundary of the treatment region may be improved compared to a boundary of a treatment region formed by the first layer of leaves.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 13A:
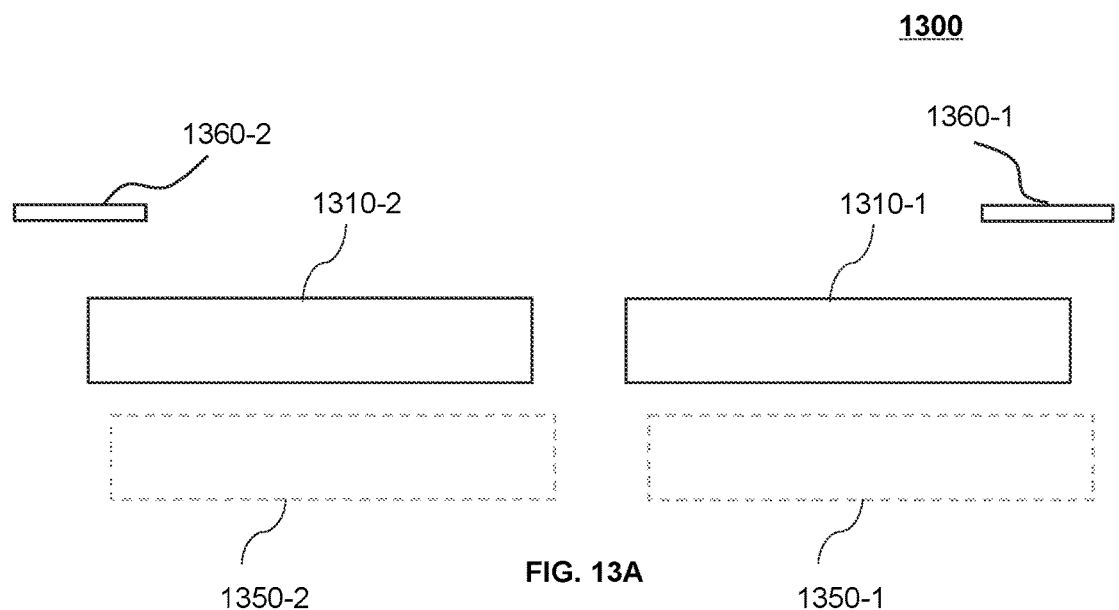
FIGS. 13A-13B are section views for operating an exemplary collimator assembly according to some embodiments of the present disclosure.
Figure 13B:
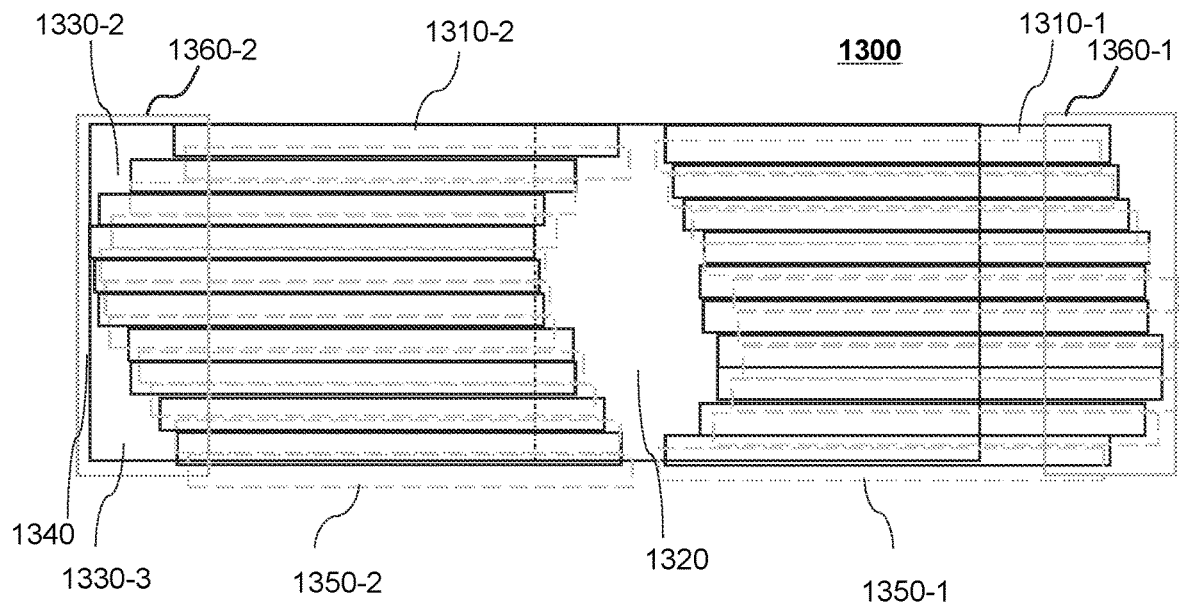

FIGS. 13A-13B are section views for operating a collimator assembly 1300 according to some embodiments of the present disclosure. The collimator assembly 1300 may be an example of the collimator assembly described in FIG. 12.

The collimator assembly 1300 may include an MLC having two layers of leaves, a first block 1360-1, and a second block 1360-2. A first layer of leaves of the MLC may include a first group of leaves 1310-1 (also referred to as "leaves 1310-1") and a second group of leaves 1310-2 (also referred to as leaves 1310-2"). A second layer of leaves of the MLC may include a first group of leaves 1350-1 (also referred to as "leaves 1350-1") and a second group of leaves 1350-2 (also referred to as leaves 1350-2"). The first block 1360-1 may be situated above the leaves 1310-1. The second block 1360-2 may be situated above the leaves 1310-2.

As illustrated in FIG. 13B, a rectangle 1340 may represent a radiation area (the maximum of the radiation area of the first radiation source 114). The two layers of leaves may be moveable to form a treatment region associated with the collimator assembly 1300. A region formed by front ends of the leaves 1310-1, the leaves 1310-2, the leaves 1350-1, and the leaves 1350-2 may constitute the treatment region, e.g., a region 1320. The projection of the two blocks along a second direction (e.g., the radiation direction 405 illustrated in FIG. 4B) of the MLC may cover a region 1330-2 and a region 1330-3, thereby blocking leaking radiation beams within a first region constituted by the region 1330-2, and the region 1330-3. In some embodiments, the collimator assembly 1300 may also include at least one jaw (not shown in FIGS. 13A-13B). For example, the projection of the at least one jaw may partially overlap the region 1320, i.e., the at least one jaw forms the treatment region associate with the collimator assembly 1300 with the MLC. The at least one jaw described herein may be similar to the jaw(s) described in FIGS. 5A, 5B, and 7A-8B, the descriptions of which may be not repeated here.

It should be noted that the above description is merely provided for the purposes of illustration, and not intended to limit the scope of the present disclosure. The count of the jaw(s) of the collimator assembly described above is non-limiting. For example, the collimator assembly may include only one jaw similar to the first jaw 750-1 (or the first jaw 850-1) or the second jaw 750-2 (or the second jaw 850-2). As another example, the collimator assembly may include multiple jaws being moveable along the first direction (e.g., the x-direction illustrated in FIG. 4). The at least one jaw may span at least a part of leaves of the MLC. In some embodiments, the thickness of each jaw may be the same as the thickness of a block illustrated in FIGS. 7A-7C or FIGS. 8A-8B. In some embodiments, the size of a jaw may be unrelated with the size of each block. For instance, at least one of the thickness, the width, or the length of a jaw may be different from or the same as the thickness, the width, or the length of a block.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:
1. A collimator assembly, comprising:
a multi-leaf collimator (MLC) situated in a first plane, the MLC comprising at least one first group of leaves and at least one second group of leaves opposing each other and being moveable along a first direction;
at least one block situated in a second plane different from the first plane, one of the at least one block being located at a position corresponding to an end of the at least one first group of leaves, and projection of one of the at least one block along a second direction partially overlapping projection of the at least one first group of leaves along the second direction; and at least one jaw situated in the second plane, the at least one jaw spanning at least a part of the at least one first group of leaves and the at least one second group of leaves, wherein the at least one jaw is movable along a third direction, and the third direction is orthogonal to the first direction and the second direction.

2. The collimator assembly of claim 1, wherein the projection of the one of the at least one block along the second direction at least covers projection of rear ends of the at least one first group of leaves along the second direction.

3. The collimator assembly of claim 1, wherein the at least one block is fixed at the position.

4. The collimator assembly of claim 1, wherein the at least one block is moveable with respect to the position.

5. The collimator assembly of claim 1, the at least one block further comprising a second block situated in the second plane, wherein the second block is located at a position corresponding to an end of the at least one second group of leaves, and projection of the second block partially overlaps projection of the at least one second group of leaves along the second direction.

6. The collimator assembly of claim 5, wherein the projection of the second block along the second direction at least covers projection of rear ends of the at least one second group of leaves along the second direction.

7. The collimator assembly of claim 1, wherein a length of each leaf of the MLC is smaller than or equal to a half of a length of a radiation area associated with the collimator assembly.

8. The collimator assembly of claim 7, wherein one or more leaves of the MLC are configured to move to a centerline of the radiation area.

9. The collimator assembly of claim 1, wherein a size of each of the at least one block relates to at least one of:

a first reference distance that at least one leaf of the at least one first group of leaves is allowed to move, a second reference distance that at least one leaf of the at least one second group of leaves is allowed to move, a width of at least one leaf of the at least one first group of leaves, a width of at least one leaf of the at least one second group of leaves, a length of at least one leaf of the at least one first group of leaves, or a length of at least one leaf of the at least one second group of leaves.

10. The collimator assembly of claim 1, wherein at least one of leaves of the MLC is movable to form a treatment region associated with the collimator assembly.

11. The collimator assembly of claim 10, wherein projection of the at least one jaw along the second direction partially overlaps the treatment region.

12. The collimator assembly of claim 11, wherein a resolution of the treatment region is adjustable by moving the at least one jaw.

13. The collimator assembly of claim 1, wherein at least one radiation non-resistant component of the collimator assembly is situated between the MLC and at least one of the at least one block or the at least one jaw.

14. The collimator assembly of claim 1, further comprising at least one second jaw being moveable along the first direction.

15. A collimator assembly, comprising:

a multi-leaf collimator (MLC) situated in a first plane, the MLC comprising at least one first group of leaves and at least one second group of leaves opposing each other and being moveable along a first direction to form a treatment region; and at least one jaw situated in a second plane different from the first plane, wherein projection of the at least one jaw along a second direction partially overlaps the treatment region, the at least one jaw is movable along a third direction, and the third direction is orthogonal to the first direction and the second direction.

16. The collimator assembly of claim 15, wherein a resolution of the treatment region is adjustable by moving the at least one jaw.

17. A method for operating a multi-leaf collimator (MLC), the method being implemented on a computing device having at least one processor and at least one computer-readable storage device, wherein:

the MLC includes at least a first layer of leaves and a second layer of leaves arranged in a second direction, each of the first layer of leaves and the second layer of leaves includes a first group of leaves and a second group of leaves, at least a portion of the leaves being movable along a first direction to form a treatment region by blocking pathways of a first portion of radiation beams within a radiation area associated with the MLC, wherein a second portion of the radiation beams impinges on the treatment region, and the method includes:

determining whether a first region except the treatment region exists, wherein the first region is formed by a rear end of one or more leaves of the first group of the first layer of leaves passing across a first line such that the first region is exposed to allow at least a portion of the first portion of the radiation beams to leak through; and in response to determining that the first region exists, causing one or more leaves of the second layer of leaves of the MLC to move to block pathways of at least a portion of leaking radiation beams within the first region.

18. The method of claim 17, wherein the MLC includes at least one jaw, the at least one jaw is movable along a third direction, and the third direction is orthogonal to the first direction and the second direction.

* * * * *